(12) United States Patent
Shimada et al.

(10) Patent No.: US 10,540,517 B2
(45) Date of Patent: Jan. 21, 2020

(54) INFORMATION PROCESSING APPARATUS, INFORMATION PROCESSING SYSTEM AND INFORMATION PROCESSING METHOD

(71) Applicant: FUJITSU LIMITED, Kawasaki-shi, Kanagawa (JP)

(72) Inventors: Yuri Shimada, Yokohama (JP); Kazunori Kobashi, Yamato (JP); Akito Yamazaki, Kawasaki (JP); Akimasa Yoshida, Nagoya (JP); Hiroyuki Katayama, Numazu (JP)

(73) Assignee: FUJITSU LIMITED, Kawasaki (JP)

(*) Notice: Subject to any disclaimer, the term of this patent is extended or adjusted under 35 U.S.C. 154(b) by 141 days.

(21) Appl. No.: 15/630,995

(22) Filed: Jun. 23, 2017

(65) Prior Publication Data
US 2018/0032754 A1    Feb. 1, 2018

(30) Foreign Application Priority Data

Jul. 26, 2016 (JP) ................................ 2016-146434
Oct. 31, 2016 (JP) ................................ 2016-213590

(51) Int. Cl.
*G06F 21/62* (2013.01)
*G06F 21/31* (2013.01)
*G16H 10/60* (2018.01)

(52) U.S. Cl.
CPC .......... *G06F 21/6245* (2013.01); *G06F 21/31* (2013.01); *G16H 10/60* (2018.01)

(58) Field of Classification Search
CPC .................................................. G06F 21/6245
See application file for complete search history.

(56) References Cited

U.S. PATENT DOCUMENTS

| 8,484,737 B1* | 7/2013 | Swift | H04L 63/1441 709/224 |
| 8,856,507 B2* | 10/2014 | Machani | G06F 21/6245 713/150 |
| 9,898,610 B1* | 2/2018 | Hadsall | G06F 21/6245 |
| 2006/0181424 A1* | 8/2006 | Graves | G01V 15/00 340/573.1 |
| 2007/0143853 A1* | 6/2007 | Tsukamoto | G06F 21/35 726/26 |
| 2009/0012816 A1 | 1/2009 | Cookson et al. | |
| 2009/0276243 A1* | 11/2009 | Fotsch | G06Q 10/10 705/2 |

(Continued)

FOREIGN PATENT DOCUMENTS

| JP | 2004-287774 | 10/2004 |
| JP | 2009-015835 | 1/2009 |

(Continued)

*Primary Examiner* — Simon P Kanaan
(74) *Attorney, Agent, or Firm* — Fujitsu Patent Center

(57) ABSTRACT

A memory stores common identification information that is shared between a plurality of information provision institutions for identifying a person. A processor assigns the common identification information to personal information transferred to a storage device from a plurality of operation databases respectively of the plurality of information provision institutions. Then, the processor generates confidentialized personal information by confidentializing the personal information to which the common identification information has been assigned.

12 Claims, 32 Drawing Sheets

(56) References Cited

U.S. PATENT DOCUMENTS

| | | | |
|---|---|---|---|
| 2010/0056883 A1* | 3/2010 | Meschisen | G16H 40/40 600/301 |
| 2010/0324934 A1* | 12/2010 | Selinfreund | G16H 10/60 705/3 |
| 2011/0239113 A1* | 9/2011 | Hung | G16H 15/00 715/271 |
| 2012/0060216 A1 | 3/2012 | Chaudhri et al. | |
| 2014/0052472 A1* | 2/2014 | Aizawa | G16H 10/60 705/3 |
| 2014/0236953 A1* | 8/2014 | Rapaport | G06Q 10/10 707/740 |
| 2015/0261921 A1* | 9/2015 | Brown, Jr. | H04L 63/08 705/3 |
| 2016/0246994 A1* | 8/2016 | Ogura | G06F 21/6245 |
| 2017/0085382 A1* | 3/2017 | Kamakari | H04L 63/0884 |
| 2017/0242963 A1* | 8/2017 | Cohen | G06F 19/00 |
| 2017/0303119 A1* | 10/2017 | Ogura | G06F 19/3418 |

FOREIGN PATENT DOCUMENTS

| | | |
|---|---|---|
| JP | 2009-266077 | 11/2009 |
| JP | 2010-128718 | 6/2010 |
| JP | 2013-537326 | 9/2013 |
| WO | 2012031052 | 3/2012 |

\* cited by examiner

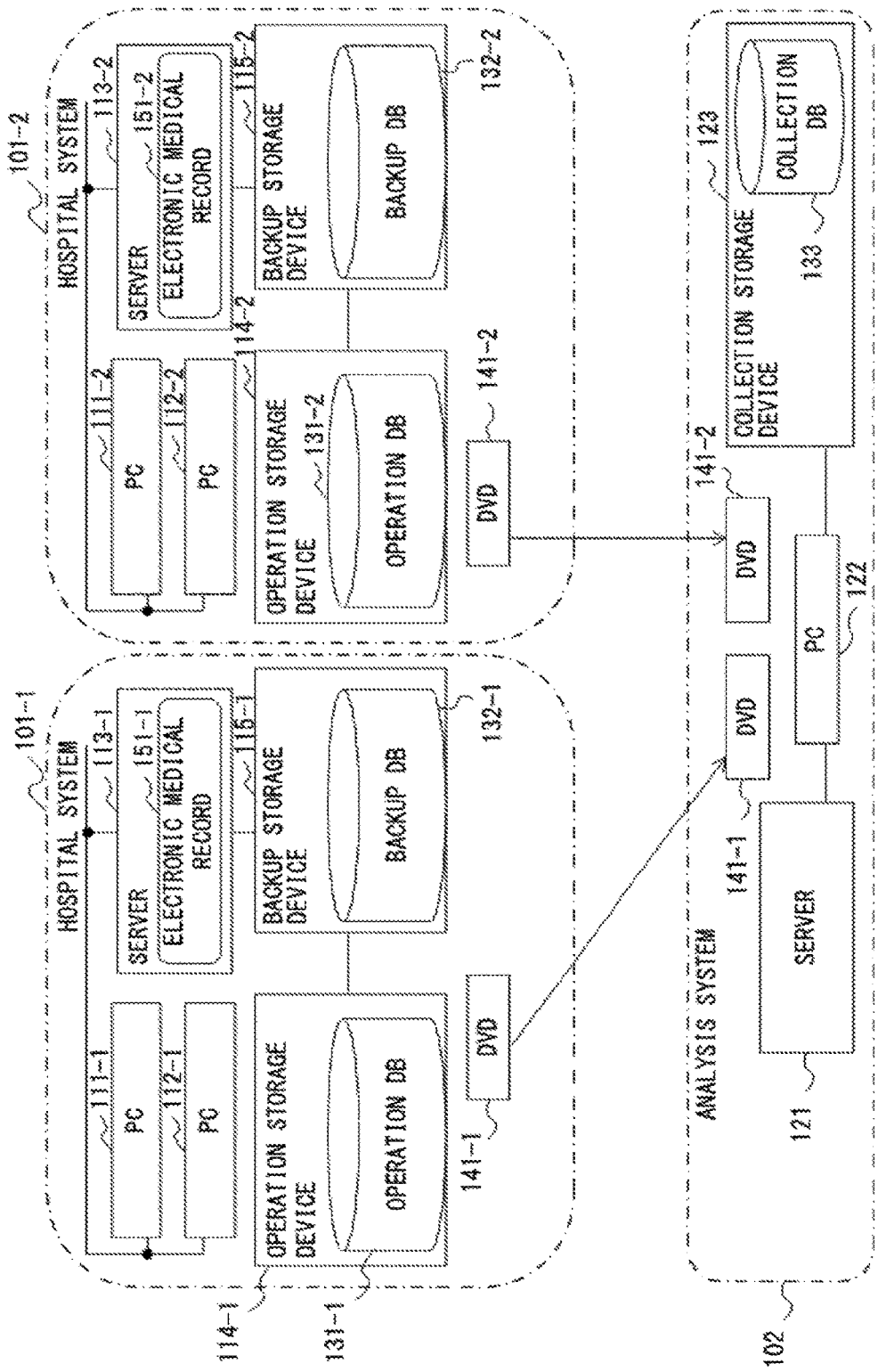
F I G. 1

| PATIENT ID | NAME | NATIONAL IDENTIFICATION NUMBER | BIRTH DATE | SEX | ADDRESS | BLOOD TYPE | HEALTH INSURANCE CARD ID | ALLERGY | TIME AND DATE OF UPDATE |
|---|---|---|---|---|---|---|---|---|---|
| 1001 | YOKOHAMA TARO | 11111234 | 1998/11/13 | MALE | 1-24-2 KOUNAN-CHO, KITA-KU, YOKOHAMA CITY | TYPE A | 132456 | ATOPY: EGG | 2016/1/3 |
| 1002 | OSAKA TARO | 504839294 | 1980/3/22 | FEMALE | 3-14-1 AOBADAI, MIDORI-KU, OSAKA CITY | TYPE B | 254326 | NONE | 2000/1/4 |
| 1003 | HAKATA ICHIRO | 392849450 | 1950/4/11 | MALE | 3 FAMILIA FUKUOKA, NINNGYOU-CHO, MINATO-KU, FUKUOKA CITY | TYPE B | 756432 | POLLEN: CEDAR | 2011/11/11 |
| 1004 | SAPPORO MICHIKO | 504938272 | 2001/9/3 | FEMALE | 4-2 ASAHIGAOKA-CHO ASAHI-KU SAPPORO CITY | TYPE O | 864326 | NONE | 2016/1/15 |

| PATIENT ID | PRESCRIPTION | EXAMINATION RESULT | DISEASE NAME | TIME AND DATE OF UPDATE |
|---|---|---|---|---|
| 1001 | GIVE INJECTION A | REDUCTION IN STOMACH MUCOUS MEMBRANE | STOMACH ULCER | 2016/1/3 |
| 1002 | ADMINISTER MEDICINE B | LUNG HAS A HOLE | LUNG PNEUMOTHORAX | 2015/10/24 |
| 1003 | ADMINISTER MEDICINE C | NOSE HAS EXCESSIVE MUCOUS MEMBRANE SUBSTANCE A | CEDAR POLLEN ALLERGY | 2015/12/20 |
| 1004 | X-RAY PHOTOGRAPH | HEART HAS A PROBLEM | HEART FAILURE | 2016/1/15 |

FIG. 10

| PATIENT ID | NAME | NATIONAL IDENTIFICATION NUMBER | BIRTH DATE | SEX | ADDRESS | BLOOD TYPE | HEALTH INSURANCE CARD ID | ALLERGY | PRESCRIPTION | EXAMINATION RESULT | DISEASE NAME |
|---|---|---|---|---|---|---|---|---|---|---|---|
| 1001 | × | × | ○ | ○ | △ | × | ○ | △ | | ○ | ○ |
| 1002 | × | × | ○ | ○ | ○ | ○ | ○ | ○ | ○ | ○ | ○ |
| 1003 | × | × | ○ | ○ | △ | × | ○ | △ | △ | △ | △ |
| 1004 | × | × | × | × | × | × | × | × | × | × | × |

| PATIENT ID | NATIONAL IDENTIFICATION NUMBER | BIRTH DATE | SEX | ADDRESS | BLOOD TYPE | HEALTH INSURANCE CARD ID | ALLERGY | PRESCRIPTION | EXAMINATION RESULT | DISEASE NAME |
|---|---|---|---|---|---|---|---|---|---|---|
| × | × | × | ○ | × | ○ | ○ | ○ | ○ | ○ | ○ |

F I G. 1 1

| COMMON ID | NATIONAL IDENTIFICATION NUMBER |
|---|---|
| ... | ... |
| 1200 | 987659 |
| 1201 | 438394 |
| 1202 | 647382 |
| 1203 | 746382 |
| 1204 | 352729 |
| 1205 | 483726 |
| ... | ... |

FIG.12

| HOSPITAL ID | CONFIDENTIALIZING COMPLETION TIME AND DATE | EQUAL-TIME SEQUENTIAL NUMBER | CONFIDENTIALIZING TARGET TIME AND DATE | PROCESS COMPLETION FLAG |
|---|---|---|---|---|
| 100 | 2015/11/5 18:55 | 3 | 2015/11/5 19:00 | true |
| 101 | 2015/10/23 04:00 | 1 | 2015/11/3 04:00 | false |
| 102 | 2015/9/31 05:00 | 2 | 2015/10/5 05:00 | false |
| 103 | 2015/10/15 19:58 | 1 | 2015/10/15 20:00 | true |

FIG.13

| HOSPITAL ID | CONFIDENTIALIZING COMPLETION TIME AND DATE | EQUAL-TIME SEQUENTIAL NUMBER | CONFIDENTIALIZING TARGET TIME AND DATE | PROCESS COMPLETION FLAG |
|---|---|---|---|---|
| 1 | 2015/05/12 23:59 | | 2015/05/20 0:00 | false |
| 2 | 2015/05/12 23:59 | | 2015/05/20 0:00 | false |
| 3 | 2015/05/12 23:59 | | 2015/05/20 0:00 | false |
| 4 | 2015/05/12 23:59 | | 2015/05/20 0:00 | false |
| ... | ... | | ... | ... |

FIG.14

| AGE | AGE GROUP |
|---|---|
| 10~19 | 10'S |
| 20~29 | 20'S |
| 30~39 | 30'S |
| 40~49 | 40'S |
| ... | ... |

FIG.15

| COMMON ID | NAME | NATIONAL IDENTIFICATION NUMBER | BIRTH DATE | SEX | ADDRESS | BLOOD TYPE | HEALTH INSURANCE CARD ID | TIME AND DATE OF UPDATE |
|---|---|---|---|---|---|---|---|---|
| 11111234 | CONFIDENTIAL INFORMATION | CONFIDENTIAL INFORMATION | 1988/11/13 | MALE | YOKOHAMA CITY | TYPE A | 132456 | 2016/1/3 |
| 11111235 | CONFIDENTIAL INFORMATION | CONFIDENTIAL INFORMATION | 1989/4/21 | FEMALE | 4-43-4 ARIAKE-CHO, HACHIOJI CITY, TOKYO METROPOLIS | TYPE B | 254326 | 2000/1/4 |
| 11111236 | CONFIDENTIAL INFORMATION | CONFIDENTIAL INFORMATION | 1950/6/15 | MALE | OITA PREFECTURE | TYPE B | 756432 | 2011/11/11 |
| 11111237 | CONFIDENTIAL INFORMATION | CONFIDENTIAL INFORMATION | CONFIDENTIAL INFORMATION | CONFIDENTIAL INFORMATION | CONFIDENTIAL INFORMATION | CONFIDENTIAL INFORMATION | CONFIDENTIAL INFORMATION | 2016/1/15 |

FIG. 16

| COMMON ID | HOSPITAL ID | PATIENT ID | PRESCRIPTION | EXAMINATION RESULT | DISEASE NAME | TIME AND DATE OF UPDATE |
|---|---|---|---|---|---|---|
| 11111234 | 98430 | 594 | SURGERY WAS CONDUCTED TO FILL HOLE | DETERMINED THAT LUNG HAS A HOLE | LUNG PNEUMOTHORAX | 2012/10/24 |
| 11111234 | 201 | 1001 | ADMINISTER MEDICINE C | REDUCTION IN STOMACH MUCOUS MEMBRANE | STOMACH ULCER | 2012/3/3 |
| 11111234 | 98430 | 594 | SURGERY WAS CONDUCTED TO FILL HOLE | HOLE WAS MADE IN LUNG AGAIN | LUNG PNEUMOTHORAX | 2014/3/9 |
| 11111234 | 201 | 1001 | WAIT-AND-SEE APPROACH | REDUCTION IN STOMACH MUCOUS MEMBRANE | STOMACH ULCER | 2015/6/24 |
| 11111234 | 201 | 1001 | ADMINISTER MEDICINE D | DAMAGES TO STOMACH DUE TO STRESS | STOMACH PAIN | 2016/9/14 |
| 11111234 | 302 | 321 | CONFIDENTIAL INFORMATION | CONFIDENTIAL INFORMATION | CONFIDENTIAL INFORMATION | 2016/12/15 |

F I G. 1 7

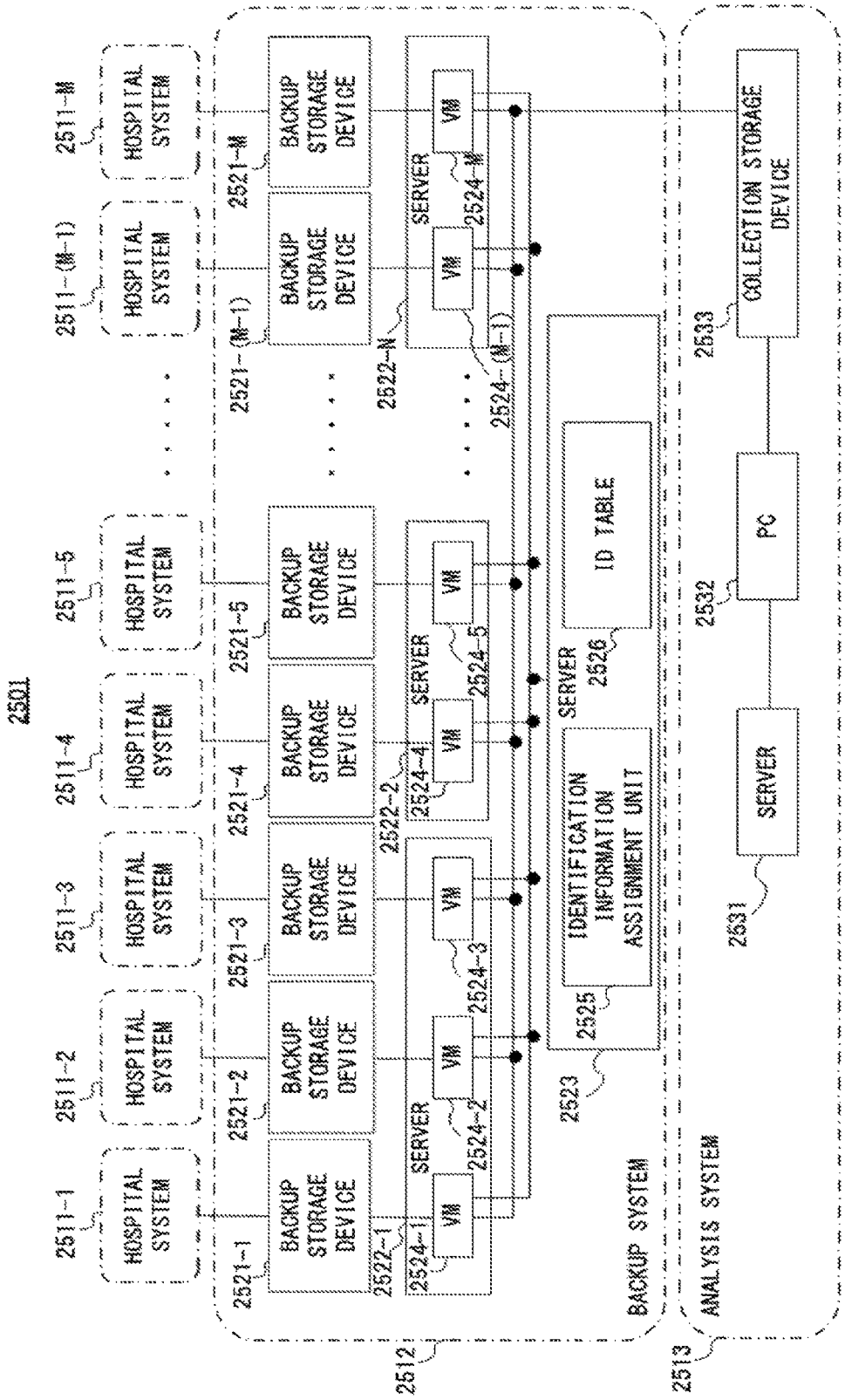
F I G. 25

| HOSPITAL ID | CONFIDENTIALIZING COMPLETION TIME AND DATE | EQUAL-TIME SEQUENTIAL NUMBER | CONFIDENTIALIZING TARGET TIME AND DATE | PROCESS COMPLETION FLAG |
|---|---|---|---|---|
| 100 | 2015/11/5 18:55 | 3 | 2015/11/5 19:00 | true |

FIG.27

INFORMATION PROCESSING APPARATUS, INFORMATION PROCESSING SYSTEM AND INFORMATION PROCESSING METHOD

CROSS-REFERENCE TO RELATED APPLICATIONS

This application is based upon and claims the benefit of priority of the prior Japanese Patent Application No. 2016-146434, filed on Jul. 26, 2016, and the Japanese Patent Application No. 2016-213590, filed on Oct. 31, 2016, the entire contents of which are incorporated herein by reference.

FIELD

The embodiments discussed herein are related to an information processing apparatus, an information processing system and an information processing method.

BACKGROUND

In recent years, there is an increasing demand for big data analysis. It is desirable to collect as many data samples as possible in order to obtain more accurate and more useful analysis results in big data analysis.

The government of Japan has a plan to carry out policy to promote big data analysis in the domestic medical field in the future. This plan aims at a situation where pieces of data of electronic medical records are collected from hospitals, the collected pieces of data are processed to anonymous data, and groups that wish to use the anonymous data are provided with the data as data available for big data analysis.

An electronic medical record is data including much personal information that is related to privacy of patients. Thus, it is desirable that a measure be taken to prevent leaks of personal information when a great amount of this kind of data is collected.

Various techniques that collect and utilize pieces of medial data such as electronic medical records are also known (see for example Patent Documents 1 through 5).

Patent Document 1: Japanese Laid-open Patent Publication No. 2010-128718
Patent Document 2: Japanese Laid-open Patent Publication No. 2004-287774
Patent Document 3: Japanese Laid-open Patent Publication No. 2009-15835
Patent Document 4: Japanese National Publication of International Patent Application No. 2013-537326
Patent Document 5: Japanese Laid-open Patent Publication No. 2009-266077

SUMMARY

According to an aspect of the embodiments, an information processing apparatus includes a memory and a processor coupled to the memory. The memory stores common identification information shared between a plurality of information provision institutions for identifying a person. The processor assigns the common identification information to personal information transferred to a storage device from a plurality of operation databases respectively of the plurality of information provision institutions. Then, the processor generates confidentialized personal information by confidentializing the personal information to which the common identification information has been assigned.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 1 illustrates a configuration of an electronic-medical-record analysis system;
FIG. 8 illustrates a basic table included in personal information;
FIG. 9 illustrates a consultation table included in the personal information;
FIG. 10 illustrates confidentializing item information used in mode M1;
FIG. 11 illustrates confidentializing item information used in mode M2;
FIG. 12 illustrates an ID table;
FIG. 13 illustrates a time-date table used in mode M1;
FIG. 14 illustrates a time-date table used in mode M2;
FIG. 15 illustrates a process table;
FIG. 16 illustrates a basic table included in confidentialized personal information;
FIG. 17 illustrates a consultation table included in the confidentialized personal information;
FIG. 25 illustrates a specific example of the second information processing system;
FIG. 27 illustrates a time-date table used in the second information processing system.

DESCRIPTION OF EMBODIMENTS

Figure 2:
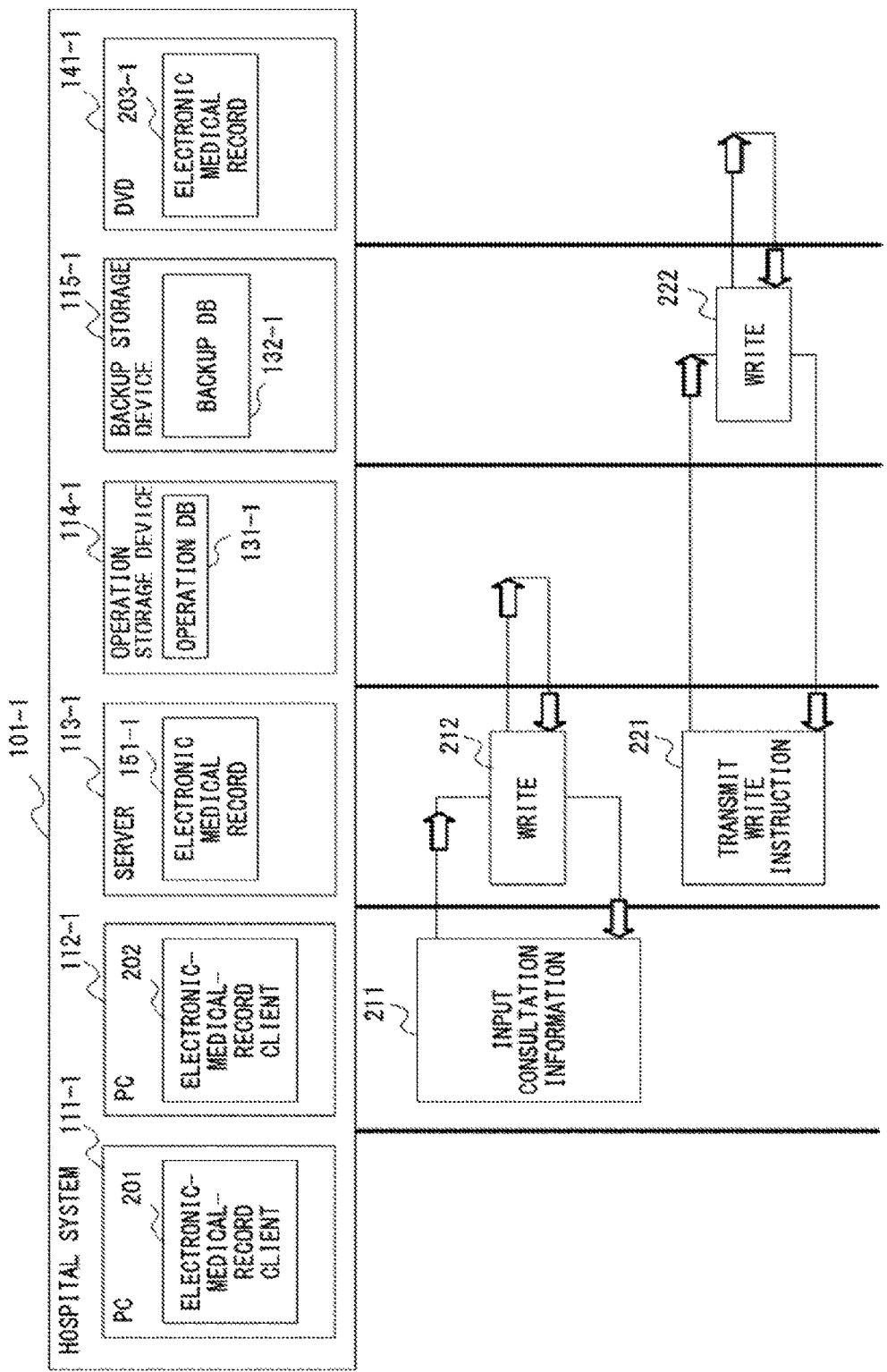
FIG. 2 illustrates a data provision sequence.

Hereinafter, detailed explanations will be given for the embodiments by referring to the drawings.

FIG. 1 illustrates a configuration example of a hypothetical electronic-medical-record analysis system that collects and analyzes electronic medical records in accordance with the policy of the government of Japan. In the electronic-medical-record analysis system illustrated in FIG. 1, an information provision institution is a hospital that provides data of electronic medical records and an information analysis institution is an institution of the government etc. that collects and analyzes data of electronic medical records.

The electronic-medical-record analysis system illustrated in FIG. 1 includes a hospital system 101-1 of hospital A, a hospital system 101-2 of hospital B and an analysis system 102 of an information analysis institution. The number of the hospital systems is not limited to two, and three or more hospital systems may exist when there are three or more hospitals. For example, a plurality of hospitals existing across the country may serve as information provision institutions.

The hospital system 101-$i$ ($i$=1, 2) includes a personal computer (PC) 111-$i$, a PC 112-$i$, a server 113-$i$, an operation storage device 114-$i$ and a backup storage device 115-$i$. The PCs 111-$i$ and 112-$i$, the server 113-$i$, the operation storage device 114-$i$ and the backup storage device 115-$i$ are connected via for example a local area network (LAN).

The server 113-$i$ stores an electronic medical record 151-$i$. The operation storage device 114-$i$ includes an operation database (DB) 131-$i$, and the backup storage device 115-$i$ includes a backup DB 132-$i$.

The analysis system 102 includes a sever 121, a PC 122 and a collection storage device 123. The collection storage device 123 includes a collection DB 133.

In the electronic-medical-record analysis system illustrated in FIG. 1, an electronic medical record is analyzed in for example the following order.

(P1) A doctor of each hospital uses the PC 111-$i$ or 112-$i$ so as to input patient's consultation information to the electronic medical record 151-$i$.

(P2) The server 113-$i$ stores the electronic medical record 151-$i$ in the operation DB 131-$i$, and the operation storage device 114-$i$ stores a copy of the electronic medical record 151-$i$ in the backup DB 132-$i$.

(P3) The system administrator of each hospital makes a digital versatile disk (DVD) 141-$i$ store a copy of the electronic medical record 151-$i$ that has been stored in the backup DB 132-$i$.

(P4) Each hospital delivers the DVD 141-$i$ to an information analysis institution.

(P5) An analyzer in the information analysis institution uses a PC 122 so as to read the electronic medical record 151-$i$ from the delivered DVD 141-$i$, and stores a copy of the electronic medical record 151-$i$ in the collection DB 133.

(P6) The analyzer uses the PC 122 so as to confidentialize the electronic medical record 151-$i$ that has been stored in the collection DB 133, and thereby generates a confidentialized electronic medical record. Thereby, the data of the electronic medical record 151-$i$ is processed to anonymous data.

(P7) The analyzer uses the PC 122 so as to analyze electronic medical records of a plurality of patients and stores the analysis results in the server 121. The analysis results are provided to information users such as research institutions, pharmaceutical companies, etc.

FIG. 2 illustrates an example of a data provision sequence in the hospital system 101-1 illustrated in FIG. 1. The PCs 111-1 and 112-1 have electronic-medical-record clients 201 and 202 installed as applications in them, respectively.

First, in accordance with manipulation from a doctor of hospital A, the electronic-medical-record client 202 inputs patient's consultation information to the electronic medical record 151-1 of the server 113-1 (step 211). Next, the server 113-1 writes the electronic medical record 151-1 to the operation DB 131-1 of the operation storage device 114-1 (step 212). Thereafter, the operation storage device 114-1 writes a copy of the electronic medical record 151-1 to the backup DB 132-1 of the backup storage device 115-1.

Next, the server 113-1 transmits a write instruction to the backup storage device 115-1 in accordance with an instruction from the system administrator of hospital A (step 221). Then, the backup storage device 115-1 writes a copy of the electronic medical record 151-1 stored in the backup DB 132-1 to the DVD 141-1 as the electronic medical record 203-1 (step 222).

In the hospital system 101-2 as well, a data provision sequence that is similar to that illustrated in FIG. 2 generates the electronic medical record 151-2 and writes a copy of the electronic medical record 151-2 to the DVD 141-2.

Figure 3:
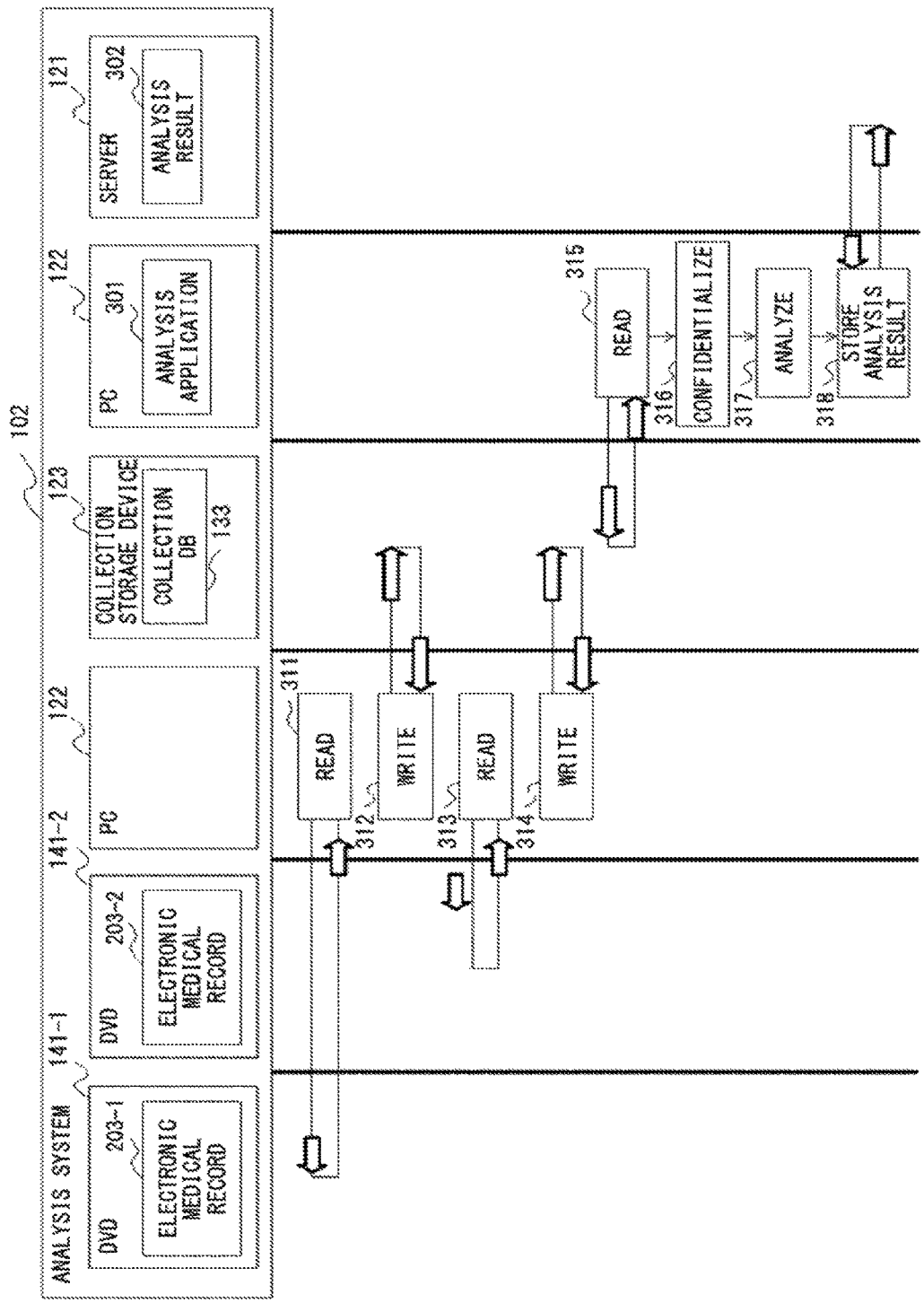
FIG. 3 illustrates a data analysis sequence.

FIG. 3 illustrates an example of a data analysis sequence in the analysis system 102 illustrated in FIG. 1. The PC 122 has an analysis application 301 installed in it.

First, in accordance with an instruction from an analyzer of an information analysis institution, the PC 122 reads the electronic medical record 203-1 from the DVD 141-1 (step 311), and writes the electronic medical record 203-1 to the collection DB 133 of the collection storage device 123 (step 312).

Next, the PC 122 reads the electronic medical record 203-2 from the DVD 141-2 in accordance with an instruction from the analyzer (step 313), and writes the electronic medical record 203-2 to the collection DB 133 (step 314).

Next, in accordance with manipulation from the analyzer, the analysis application 301 reads the electronic medical records 203-1 and 203-2 from the collection DB 133 (step 315). Then, the analysis application 301 confidentializes the electronic medical records 203-1 and 203-2 so as to generate a confidentialized electronic medical record (step 316).

Next, in accordance with manipulation from the analyzer, the analysis application 301 analyzes confidentialized electronic medical records of a plurality of patients (step 317) and stores analysis results 302 in the server 121 (step 318).

In the electronic medical record analysis system illustrated in FIG. 1, the analyzer of an information analysis institution that manages the collection DB 133 is eligible to directly treat electronic medical records which are not confidentialized, and the analyzer himself or herself is entrusted with the operation of confidentializing electronic medical records. This leads to anxiety among patients about the protection of their personal information, resulting in an increase in hospitals that refuse to provide electronic medical records to an information analysis institution, which makes it difficult to collect data in a sufficient amount for big data analysis.

Also, because a plurality of hospitals independently generate electronic medical records and provide them to an information analysis institution, electronic medical records of the same patient who received consultations in a plurality of hospitals will be stored in the collection DB 133 as electronic medical records of different patients. This results in a possibility that an inaccurate analysis result, which is different from a result that would be obtained in a case where such electronic medical records are treated as those of the same patient, will be obtained.

Note that this problem arises not only in a case when electronic medical records of hospitals are collected, but also in a case when other types of personal information are collected in other types of information provision institutions.

Figure 4:
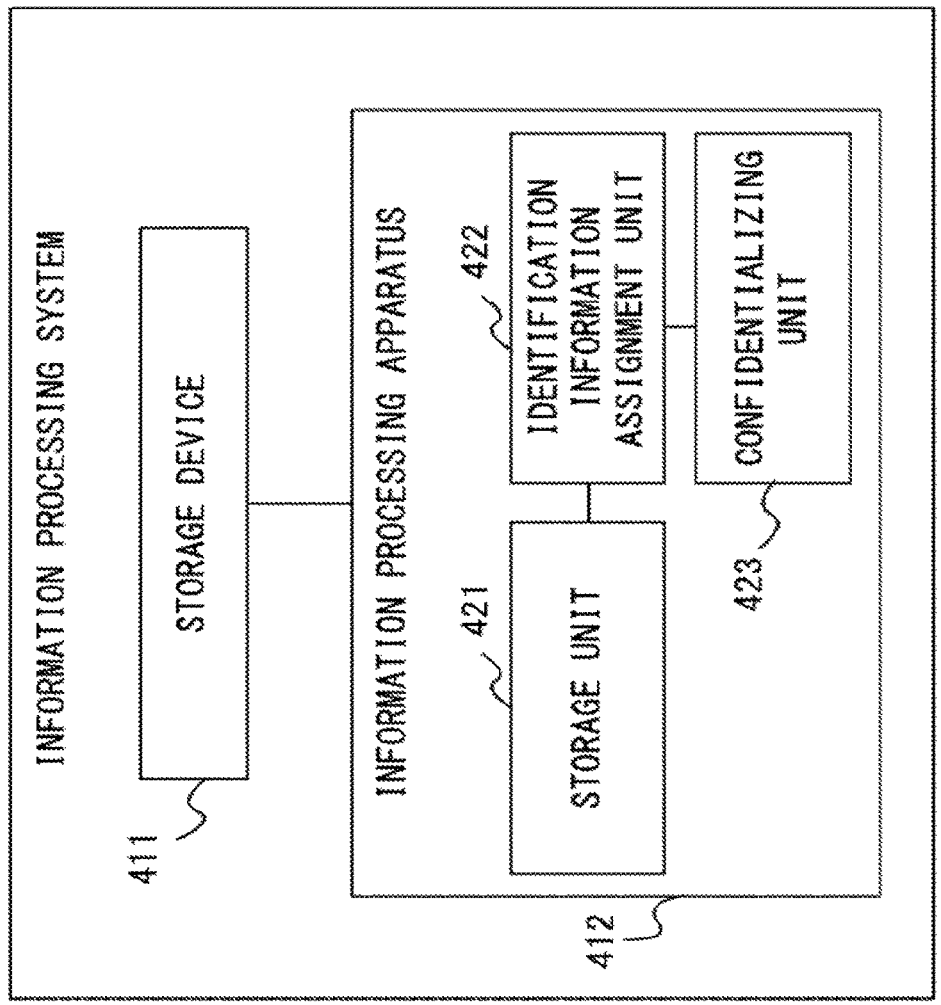
FIG. 4 illustrates a configuration of a first information processing system.

FIG. 4 illustrates a configuration example of a first information processing system of an embodiment. An information processing system 401 illustrated in FIG. 4 includes a storage device 411 and an information processing apparatus 412 (computer), and the information processing apparatus 412 includes a storage unit 421, an identification information assignment unit 422 and a confidentializing unit 423.

The storage device 411 stores personal information transferred from a plurality of operation databases respectively of a plurality of information provision institutions. The storage unit 421 of the information processing apparatus 412 stores common identification information that is shared between the plurality of information provision institutions for identifying a person. The identification information assignment unit 422 and the confidentializing unit 423 use the common identification information so as to perform a confidentializing process.

Figure 5:
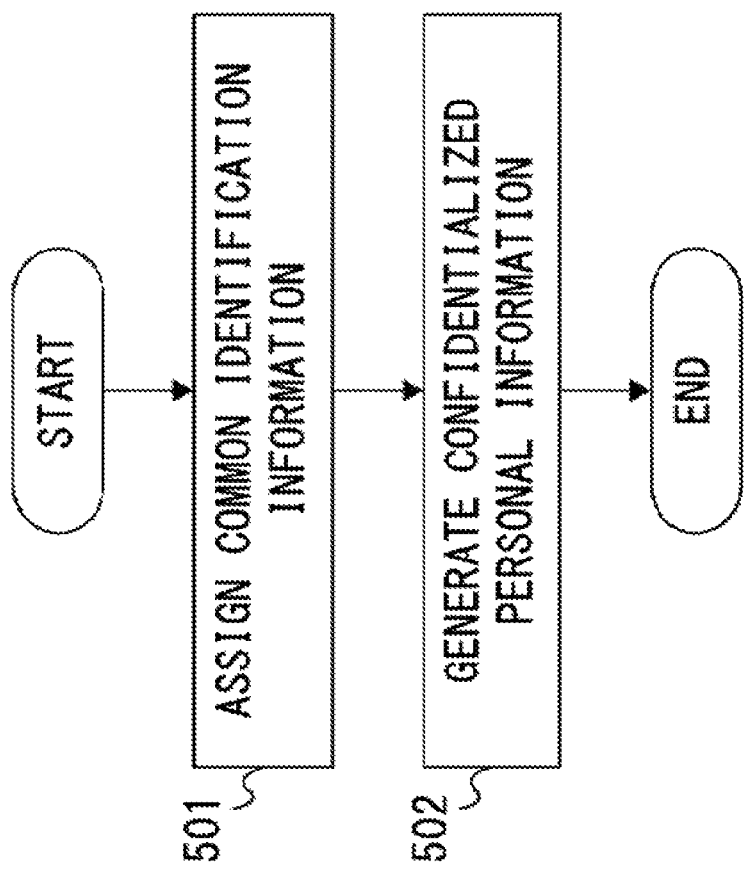
FIG. 5 is a flowchart illustrating a first confidentializing process.

FIG. 5 is a flowchart illustrating an example of a first confidentializing process that is performed by the information processing apparatus 414 illustrated in FIG. 4. First, the identification information assignment unit 422 assigns the common identification information to the personal information stored in the storage device 411 (step 501). Then, the confidentializing unit 423 confidentializes the personal information to which the common identification information has been assigned, and generates confidentialized personal information (step 502).

This information processing system 401 makes it possible to identify pieces of information of the same person from among pieces of confidentialized personal information that has been obtained by confidentializing personal information collected from a plurality of information provision institutions. Hereinafter, identification information may also be referred to as an ID.

Figure 6:
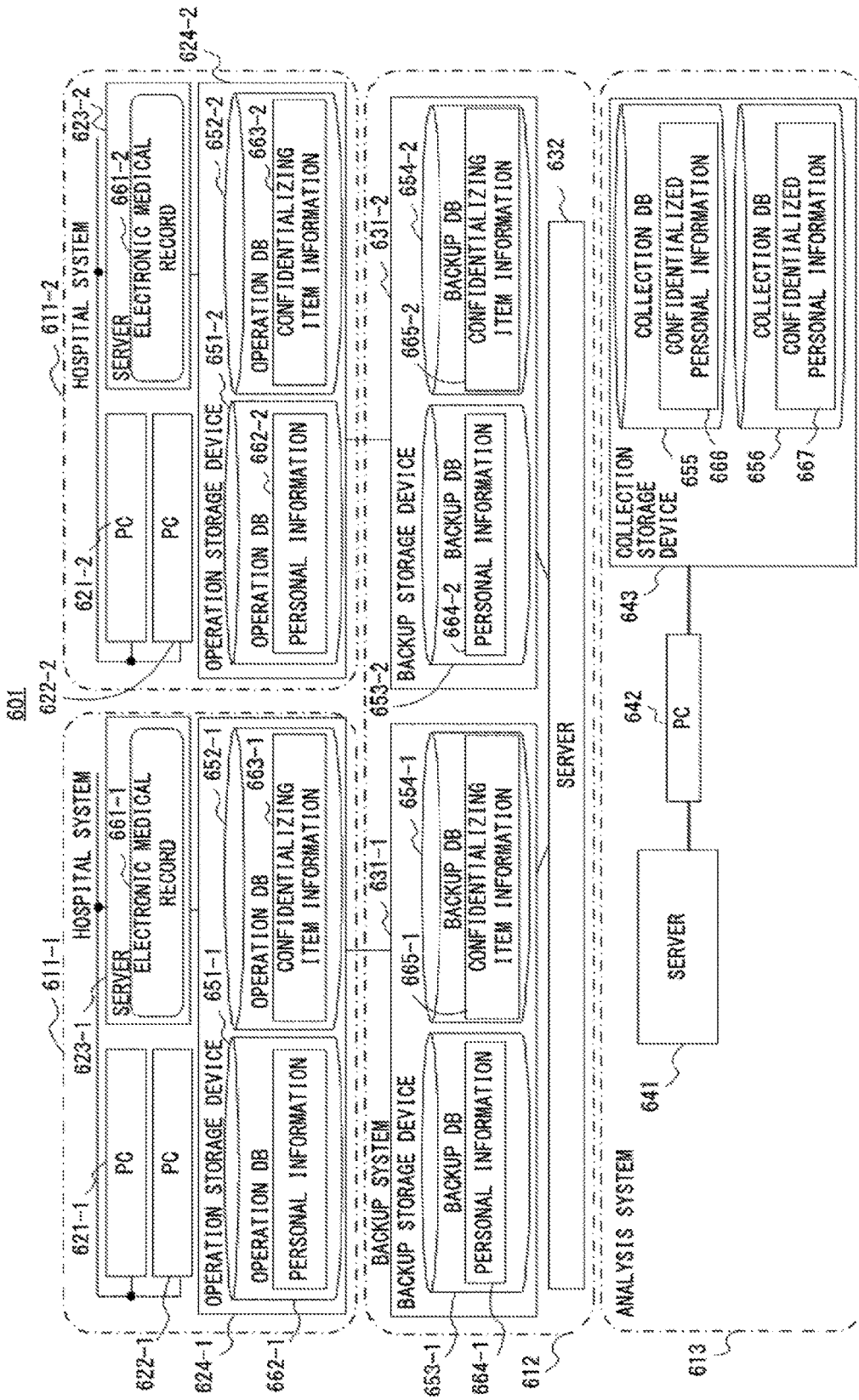
FIG. 6 illustrates a specific example of the first information processing system.

FIG. 6 illustrates a specific example of the information processing system 401 illustrated in FIG. 4. An information processing system 601 illustrated in FIG. 6 includes a hospital system 611-1 of hospital A, a hospital system 611-2 of hospital B, a backup system 612 and an analysis system 613 of an information analysis institution. Similarly to the electronic medical record analysis system illustrated in FIG. 1, there may be three or more hospital systems.

The hospital system 611-i (i=1, 2) includes a PC 621-i for a staff member, a PC 622-i for a doctor, a server 623-i and an operation storage device 624-i of each hospital. The PC 621-i, the PC 622-i, the server 623-i and the operation storage device 624i are connected via for example a LAN.

The server 623-i stores an electronic medical record 661-i. The operation storage device 624-i includes an operation DB 651-i and an operation DB 652-i. The operation DB 651-i stores personal information 662-i, and the operation DB 652-i stores confidentializing item information 663-i.

The personal information 662-i is consultation information of the patient stored in electronic medical record 661-i, and the confidentializing item information 663-i is information that specifies an item as a confidentializing target from among a plurality of items included in the personal information 662-i. An item as a confidentializing target is specified for example by the patient himself or herself, and is applied to the personal information 662-i of that patient.

The backup system 612 is provided on for example a backup site in a communication network such as the Internet etc., and includes a backup storage device 631-1, a backup storage device 631-2 and a server 632. The backup storage device 631-1 and the backup storage device 631-2 correspond to the storage device 411 illustrated in FIG. 4, and the server 632 corresponds to the information processing apparatus 412.

The backup storage device 631-1 includes a backup DB 653-1 and a backup DB 654-1 of hospital A, and the backup storage device 631-2 includes the a backup DB 653-2 and a backup DB 654-2 of hospital B.

The backup DB 653-i stores the personal information 664-i, and the backup DB 654-i stores confidentializing item information 665-i. The personal information 664-i and the confidentializing item information 665-i are copies respectively of the personal information 662-i and the confidentializing item information 663-i.

The analysis system 613 includes a server 641, a PC 642 and a collection storage device 643. The collection storage device 643 includes a collection DB 655 and a collection DB 656, the collection DB 655 stores confidentialized personal information 666, and the collection DB 656 stores confidentialized personal information 667.

Figure 7:
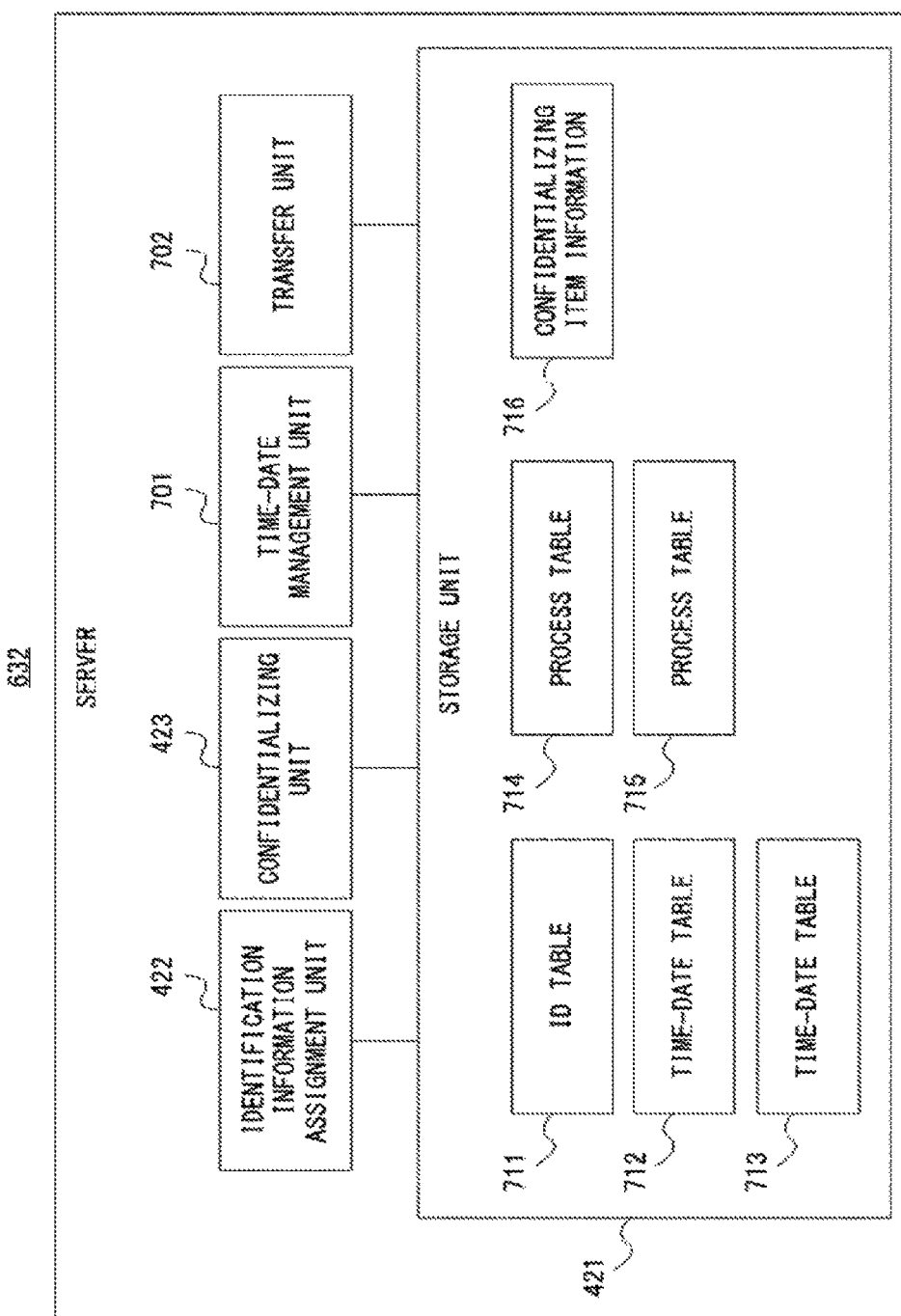
FIG. 7 illustrates a functional configuration of a server.

FIG. 7 illustrates a functional configuration example of the server 632 illustrated in FIG. 6. The server 632 illustrated in FIG. 7 includes the storage unit 421, the identification information assignment unit 422, the confidentializing unit 423, a time-date management unit 701 and a transfer unit 702. The storage unit 421 stores an ID table 711, a time-date table 712, a time-date table 713, a process table 714, a process table 715 and confidentializing item information 716.

The ID table 711 includes a correspondence relationship that associates personal identification information (personal ID) included in the personal information 664-i and common identification information (common ID). The time-date table 712 and the time-date table 713 include a target time and date and a completion time and date of a confidentializing process for the personal information 664-i. The process tables 714 and 715 are tables for converting information of a particular item included in the personal information 664-i into simplified information, and includes a correspondence relationship associating the information before conversion and information after conversion.

The confidentializing item information 716 is information that specifies an item as a confidentializing target from among a plurality of items included in the personal information 664-i. An item as a confidentializing target included in the confidentializing item information 716 is specified by for example an institution such as the government that is not a patient.

The identification information assignment unit 422 refers to the ID table 711 so as to assign a common ID corresponding to a personal ID included in the personal information 664-i to the personal information 664-i. The confidentializing unit 423 confidentializes the personal information 664-i to which a common ID has been assigned, and thereby generates the confidentialized personal information 666 and confidentialized personal information 667. The time-date management unit 701 updates entries on the time-date table 712 and the time-date table 713, and the transfer unit 702 transfers the confidentialized personal information 666 and the confidentialized personal information 667 to the collection storage device 643.

The information processing system 601 illustrated in FIG. 6 can perform an operation of mode M1, which performs a confidentializing process in accordance with a request from each hospital, and an operation of mode M2, which performs a confidentializing process in accordance with a request from an information analysis institution. In mode M1, the server 632 uses the time-date table 712, the process table 714 and the confidentializing item information 665-*i* so as to perform a confidentializing process for the personal information 664-*i*. In mode M2, the server 632 uses the time-date table 713, the process table 715 and the confidentializing item information 716 so as to perform a confidentializing process for the personal information 664-*i*.

FIG. 8 illustrates an example of a basic table included in the personal information 662-*i* and the personal information 664-*i*. The basic table illustrated in FIG. 8 is a table registering basic information of patients, and includes patient ID, name, national identification number, birth date, sex, address, blood type, health insurance card ID, allergy and time and date of update. An patient ID is an ID assigned to a patient by each hospital, and a national identification number is an ID assigned to citizens by the government, an health insurance card ID is an ID assigned to an insured person by an insurer. A time and date of update represents a time and date at which the basic information of each patient was updated.

FIG. 9 illustrates an example of a consultation table included in the personal information 662-*i* and the personal information 664-*i*. The consultation table illustrated in FIG. 9 is a table registering consultation information of patients, and includes items of patient ID, prescription, examination result, name of disease, and time and date of update. Prescription represents prescription given through a consultation, an examination result represents an examination result that was referred to during a consultation, and name of disease represents the name of a disease determined in a consultation. A time and date of update represents a time and date at which consultation information of each patient was updated.

FIG. 10 illustrates an example of the confidentializing item information 655-*i* used in mode M1. Each entry of the confidentializing item information 665-*i* illustrated in FIG. 10 corresponds to personal information of each patient included in the basic table illustrated in FIG. 8 and the consultation table illustrated in FIG. 9, and includes one of symbols of "○", "Δ" and "x".

"○" represents information that can be provided without being confidentialized, "Δ" represents information that can be provided when it is processed so that the individual person is not identified, and "x" represents information that will not be provided at all. Items for which "Δ" or "x" is set correspond to items as confidentializing targets. The information of an item for which "Δ" is set is converted into simplified information by using the process table 714 or the process table 715, and the information of an item for which "x" is set is converted into data representing that information has been confidentialized.

In the information processing system 601, scopes in which information can be provided and methods of the provision may vary depending upon how each patient treats his or her personal information or upon the characteristics of his or her disease. For example, the confidentializing item information having a patient ID of "1001" has "○" set for the birth date, the sex, the health insurance card ID, the prescription, the examination result and the name of disease. Also, the information has "x" set for the name, the national identification number and the blood type, and has "Δ" set for the address and the allergy.

By contrast, the confidentializing item information having a patient ID of "1004" has "x" set for all the items.

FIG. 11 illustrates an example of the confidentializing item information 716 used in mode M2. The confidentializing item information 716 illustrated in FIG. 11 is applied to the personal information 664-*i* of all patients. In this example, "○" is set for the sex, the blood type, the health insurance card ID, allergy, the prescription, the examination result and the name of disease, while "x" is set for the name, the national identification number, the birth date and the address.

FIG. 12 illustrates an example of the ID table 711. The ID table 711 illustrated in FIG. 12 includes common IDs and national identification numbers, and represents a correspondence relationship that associates a national identification number, which is an personal ID included in the personal information 664-*i*, and a common ID, which is shared between a plurality of hospitals for identifying a person.

FIG. 13 illustrates an example of the time-date table 712 used in mode M1. The time-date table 712 illustrated in FIG. 13 includes hospital IDs, confidentializing completion times and dates, equal-time sequential numbers, confidentializing target times and dates, and process completion flags. An hospital ID is an ID for identifying a hospital, and a confidentializing completion time and date is a time and date that represents the progress of a confidentializing process for the personal information 664-*i*. Each time the personal information 664-*i* of one patient on the basic table illustrated in FIG. 8 and the consultation table illustrated in FIG. 9 is confidentialized for example, the time and date of update of that piece of personal information 664-*i* is copied into the confidentializing completion time and date.

An equal-time sequential number represents an order of the personal information 664-*i* for which a confidentializing process has been completed from among the plurality of pieces of personal information 664-*i* having the same time and date of update. An equal-time sequential number of "3" for example represents that a confidentializing process has been completed for up to the third pieces of personal information 664-*i* from among the plurality of pieces of personal information 664-*i* having the time and date of update copied into the confidentializing completion time and date. In such a case, a confidentializing process has not been completed for the fourth and subsequent pieces of personal information 664-*i*.

A confidentializing target time and date is a time and date that specifies a scope of the personal information 664-*i* as a target of a confidentializing process. Pieces of the personal information 664-*i* having an time and date of update that is equal to or earlier than the confidentializing target time and date become a target of a confidentializing process. A process completion flag represents whether or not a confidentializing process has been completed for the pieces of personal information 664-*i* updated earlier than the confidentializing target time and date in each hospital and the piece of personal information 664-*i* updated at the confidentializing target time and date. When a confidentializing target time and date is set in the time-date table 712, the process completion flag is set to "false", and when a confidentializing process has been completed for the pieces of personal information 664-*i* updated earlier than the confidentializing target time and date and the piece of personal information 664-*i* updated at the confidentializing target time and date, the process completion flag is set to "true".

FIG. 14 illustrates an example of the time-date table 713 used in mode M2. When a collection period of the personal information 664-*i* is specified by a request from an information analysis institution, the time-date management unit 701 sets a confidentializing completion time and date and a confidentializing target time and date on the time-date table 713 on the basis of the collection starting time and date and the collection ending time and date. In this case, the time-date management unit 701 sets confidentializing completion time and dates corresponding to all the hospital IDs to the same time and date, and sets confidentializing target time and dates corresponding to all the hospital IDs to the same time and date.

For example, when the collection starting time is "May 13, 2015 0:00", "May 12, 2015 23:59", which is one second earlier than the collection starting time, is set as the confidentializing completion time and date. Also, when the collection ending time is "May 20, 20150 0:00", "May 20, 2015 0:00", which is equal to the collection ending time, is set as the confidentializing target time and date.

FIG. 15 illustrates an example of the process table 714 that is used in mode M1 and the process table 715 that is used in mode M2. The process table illustrated in FIG. 15 includes age and age group, and represents a correspondence relationship that associates an age that is information before conversion and an age group that is information after conversion. An age can be calculated from the birth date included in the basic table illustrated in FIG. 8. Using the process table illustrated in FIG. 15 simplifies information of a birth date that allows the identification of a person into information of an age group that is anonymous data.

Also, when an item that is to be simplified is an address, a process table may be use for deleting, from the character string of the address, the name of a town, a block number, etc. that allow the identification of a person. This can simplify an address of "1-24-2, Kounan-cho, Kita-ku, Yokohama-shi" into "Yokohama-shi".

FIG. 16 illustrates an example of a basic table included in the confidentialized personal information 666 and the confidentialized personal information 667. The basic table illustrated in FIG. 16 includes items of common ID, name, national identification number, birth date, sex, address, blood type, health insurance card ID and time and date of update. A common ID is a common ID that is assigned by the identification information assignment unit 422.

In this example, the names and the national identification numbers of all the patients have been converted into a character string of "confidential information", which is data representing that information has been confidentialized. Also, the address of the patient of a common ID of "11111234" has been converted into "Yokohama-shi" as a simplified character string, and the information of all the items of the patient of a common ID of "11111237" has been converted into a character string of "confidential information".

FIG. 17 illustrates an example of a consultation table included in the confidentialized personal information 666 and the confidentialized personal information 667. The consultation table illustrated in FIG. 17 includes items of common ID, hospital ID, patient ID, prescription, examination result, name of disease and time and date of update.

In this example, the patient of a common ID of "11111234" has been registered as a patient of a patient ID of "594" in the hospital of a hospital ID of "98430", and has been registered as a patient of a patient ID of "1001" in the hospital of a hospital ID of "201". Also, that patient has been registered as a patient of a patient ID of "321" in the hospital of a hospital ID of "302". Also, the prescription, the examination result and the name of disease have been converted into a character string of "confidential information" in the hospital of a hospital ID of "302".

As described above, assigning a common ID to the confidentialized personal information 666 and the confidentialized personal information 667 makes it possible to identify pieces of information of the same patient from among pieces of confidentialized personal information collected from a plurality of hospitals.

Incidentally, hospitals A and B do not always have the personal information 664-1 and the personal information 664-2 in the same data format. When the personal information 664-1 and the personal information 664-2 are in different data formats, the confidentializing unit 423 converts the data formats of pieces of personal information 664-$i$ into a uniform data format, and generates the confidentialized personal information 666 and the confidentialized personal information 667 from the converted personal information. This makes it possible to compensate for differences in data formats between hospitals.

For example, the server 623-$i$ of each hospital system 611-$i$ generates a conversion program for converting the data format of personal information 662-$i$ in the operation DB 651-$i$ into the uniform data format, and transmits the program to the backup system 612 in advance. Then, the confidentializing unit 423 of the server 632 uses the received conversion program so as to convert the data format of the personal information 664-$i$ into the uniform data format.

Figure 18:
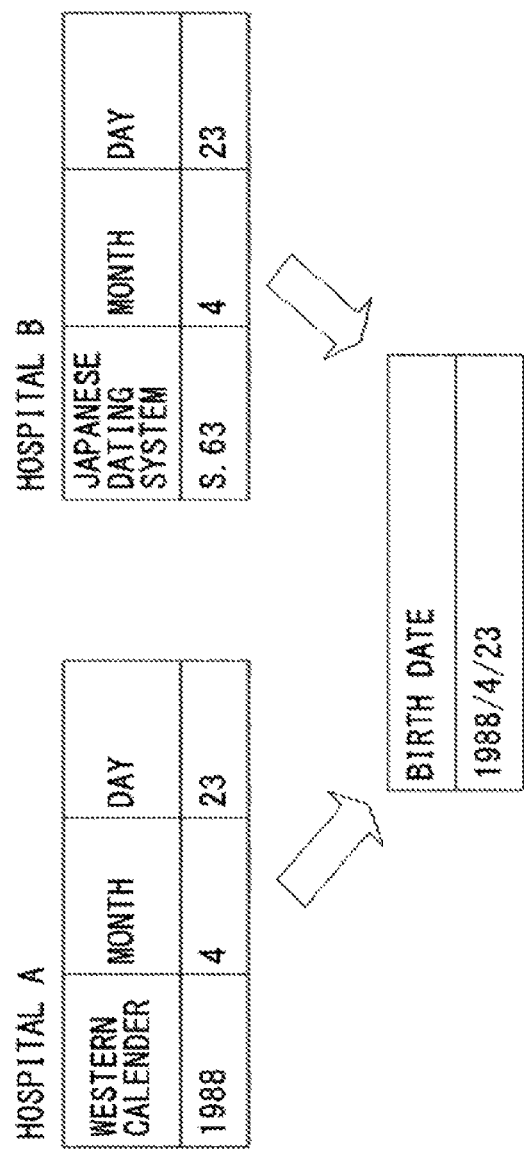
FIG. 18 illustrates a process of converting a data format.

FIG. 18 illustrates an example of a process of converting a data format. In this example, "year", "month" and "day" are described in separate columns as information of the birth date in the personal information 664-$i$ of hospitals A and B. Among them, the personal information 664-1 of hospital A has the information of "year" described in the Western calendar, while the personal information 664-2 of hospital B has the same information described in the Japanese dating system.

When the personal information 664-1 of hospital A is to be converted, the confidentializing unit 423 extracts character strings from the columns respectively of "year (Western calendar), "month" and "day" in the personal information 664-1. Then, the confidentializing unit 423 uses the conversion program received from the server 623-1 so as to connect the character strings to each other with slashes, and generates a character string of "birth date" in the uniform data format.

When the personal information 664-2 of hospital B is to be converted, the confidentializing unit 423 extracts character strings from the columns respectively of "year (Japanese dating system), "month" and "day" in the personal information 664-2. Then, the confidentializing unit 423 uses the conversion program received from the server 623-2 so as to convert the character string of the year in the Japanese dating system into a character string in the Western calendar and connects the character strings to each other with slashes, and generates a character string of "birth date" in the uniform data format.

When the information processing system 601 illustrated in FIG. 6 operates in mode M1, an electronic medical record is analyzed for example in the following order.

(P11) A staff member or a patient of each hospital uses the PC 621-$i$ so as to input, to the electronic medical record 661-$i$, confidentializing item information that the patient wants to be confidential. Confidentializing item information can be changed in accordance with a request from the patient after being input at the first consultation.

(P12) The server 623-$i$ stores the input confidentializing item information in the operation DB 652-$i$ as the confidentializing item information 663-$i$.

(P13) A doctor in each hospital uses the PC 622-$i$ so as to input consultation information of a patient to the electronic medical record 661-$i$.

(P14) The server 623-*i* stores the input consultation information in the operation DB 651-*i* as the personal information 662-*i*.

(P15) A system administrator in each hospital makes a backup periodically. Then, the operation storage device 624-*i* transfers copies of the personal information 662-*i* and the confidentializing item information 663-*i* to the backup storage device 631-*i*. Then, the backup storage device 631-*i* stores a copy of the personal information 662-*i* in the backup DB 653-*i* as the personal information 664-*i*, and stores a copy of the confidentializing item information 663-*i* in the backup DB 654-*i* as the confidentializing item information 665-*i*.

(P16) The server 623-*i* transmits a confidentializing request to the server 632 periodically, and the time-date management unit 701 of the server 632 sets the confidentializing target time and date in the time-date table 712 on the basis of the confidentializing request.

(P17) The confidentializing unit 423 inquires of the time-date management unit 701 about whether or not to perform a confidentializing process. The time-date management unit 701 refers to a confidentializing completion time and date and a confidentializing target time and date on the time-date table 712 so as to transmit a response specifying whether or not to perform a confidentializing process to the confidentializing unit 423.

(P18) When a confidentializing process is to be performed, the confidentializing unit 423 obtains a confidentializing completion time and date from the time-date table 712 and searches the personal information 664-*i* for an entry having a time and date of update that is later than the confidentializing completion time and date.

(P19) The confidentializing unit 423 uses a conversion program of each hospital so as to convert the data format of each entry of the personal information 664-*i* into the uniform data format.

(P20) The identification information assignment unit 422 refers to the ID table 711 so as to assign a common ID corresponding to a personal ID included in each entry of the personal information 664-*i* to that entry.

(P21) The confidentializing unit 423 refers to the confidentializing item information 655-*i* of a patient corresponding to each entry, and confidentializes the information of an item as a confidentializing target so as to generate the confidentialized personal information 666. Then, a hospital ID is assigned to each entry of the confidentialized personal information 666. When for example the confidentializing item information 665-*i* illustrated in FIG. 10 is used, the information of an item for which "○" is set is not converted, while the information of an item for which "Δ" is set is converted into simplified information by using the process table 714. Also, the information of an item for which "x" is set is converted into data representing that information has been confidentialized.

(P22) The transfer unit 702 transfers the confidentialized personal information 666 to the collection storage device 643, and the collection storage device 643 stores the confidentialized personal information 666 in the collection DB 655.

(P23) An analyzer in an information analysis institution uses the PC 642 so as to analyze the confidentialized personal information 666 and stores the analysis result in the server 641. The analysis results are provided to information users such as research institutions, pharmaceutical companies, etc.

When the information processing system 601 illustrated in FIG. 6 operates in mode M2, an electronic medical record is analyzed for example in the following order.

(P31) The hospital system 611-*i* performs similar operations to (P11) through (P15) in mode M1.

(P32) An analyzer in an information analysis institution uses the PC 642 and transmits an information provision request to the server 632 together with the process table 715 and the confidentializing item information 716.

(P33) The confidentializing unit 423 switches from the process table 714 to the process table 715 as a process table that is to be referred to in a confidentializing process.

(P34) The confidentializing unit 423 switches from the confidentializing item information 665-*i* to the confidentializing item information 716 as confidentializing item information that is to be referred to in a confidentializing process.

(P35) The time-date management unit 701 sets a confidentializing completion time and date and a confidentializing target time and date on the time-date table 713 on the basis of a collection period specified by an information provision request.

(P36) The confidentializing unit 423 switches from the time-date table 712 to the time-date table 713 as a time-date table that is to be referred to in a confidentializing process.

(P37) The confidentializing unit 423 obtains the confidentializing completion time and date from the time-date table 713 so as to search the personal information 664-1 and the personal information 664-2 for an entry having a time and date of update that is later than the confidentializing completion time and date.

(P38) The confidentializing unit 423 uses a conversion program in each hospital so as to convert the data format of each entry of the personal information 664-1 and the personal information 664-2 into the uniform data format.

(P39) The identification information assignment unit 422 refers to the ID table 711 so as to assign a common ID corresponding to a personal ID included in each entry of the personal information 664-1 and the personal information 664-2 to that entry.

(P40) The confidentializing unit 423 refers to confidentializing item information 716 so as to grant confidentiality to the information of an item as a confidentializing target, and generates the confidentialized personal information 667. Then, a hospital ID is assigned to each entry of the confidentialized personal information 667.

(P41) The transfer unit 702 transfers the confidentialized personal information 667 to the collection storage device 643, and the collection storage device 643 stores the confidentialized personal information 667 in the collection DB 656.

(P42) An analyzer of an information analysis institution uses the PC 642 so as to analyze the confidentialized personal information 667 and stores the analysis result in the server 641.

The above information processing system 601 will provide effects as follows.

(1) Provision of the backup system 612 that performs a confidentializing process in a backup site in a communication network makes it possible to confidentialize the personal information 664-*i* independently from the operation of the hospital system 611-*i*. Thereby, each hospital does not have to newly provide a mechanism that performs a confidentializing process, avoiding loads on the business operation.

(2) No analyzers in an information analysis institution directly treats the personal information 664-*i* that has not been confidentialized, making it possible for patients and hospitals to provide information without having a sense of resistance about the protection of personal information. Thus, it is possible to collect pieces of data in a sufficient amount for big data analysis, permitting to obtain more desirable analysis results.

(3) Even when the same patient received consultation in a plurality of hospitals, it is possible to identify information of that same patient from among pieces of confidentialized personal information collected from a plurality of hospitals by assigning a common ID to the confidentialized personal information 666 and the confidentialized personal information 667. This makes it possible to collect pieces of information of the same patient notwithstanding boarders between different hospitals, and thereby more accurate analysis results can be obtained.

(4) Using a different piece of the confidentializing item information 663-*i* for each patient makes it possible to perform a confidentializing process that is tailored to each patient.

(5) Providing a confidentializing process in mode M1, which is based on a request from each hospital, and mode M2, which is based on a request from an information analysis institution, makes it possible to collect pieces of the personal information 664-*i* while reflecting intentions of information analysis institutions flexibly.

(6) Using a conversion program provided by each hospital to convert the personal information 664-*i* into the uniform data format makes it possible to generate the confidentialized personal information 666 and the confidentialized personal information 667 even when the hospitals use different data formats.

For example, the information processing system 601 performs a confidentializing process in mode M1 under a normal state, and preferentially performs a confidentializing process in mode M2 when receiving a request from an information analysis institution at a time of emergency. In such a case, the information processing system 601 interrupts confidentializing processes for all hospitals and starts confidentializing process in mode M2.

After completion of the confidentializing process in mode M2, the information processing system 601 restarts the confidentializing process in mode M1 from the location of the interruption in the personal information 664-*i*. This makes it possible to confidentialize all pieces of personal information 664-*i* in a period of time shorter than in a case when a confidentializing process is restarted from the first entry in the personal information 664-*i*.

Specifically, when interrupting a confidentializing process in mode M1, the confidentializing unit 423 switches from the time-date table 712, the process table 714 and the confidentializing item information 665-*i* to the time-date table 713, the process table 715 and the confidentializing item information 716. Further, the confidentializing unit 423 switches from the collection DB 655 to the collection DB 656.

When restarting a confidentializing process in mode M1, the confidentializing unit 423 switches from the time-date table 713, the process table 715 and the confidentializing item information 716 to the time-date table 712, the process table 714 and the confidentializing item information 665-*i*, which had been used until the previous switching. Further, the confidentializing unit 423 switches from the collection DB 656 to the collection DB 655, which had been used until the previous switching.

As described above, automatically switching resources used for a confidentializing process upon interruption of a confidentializing process and reusing the original resource upon the restart of the confidentializing process makes it easy to restart the interrupted confidentializing process.

Also, providing a process completion flag in the time-date table 712 to record whether or not a confidentializing process has been completed in each hospital makes it possible to identify a hospital that interrupted a confidentializing process. Further, recording a confidentializing completion time and date and an equal-time sequential number in the time-date table 712 makes it clear up to which of the entries included in the personal information 664-*i* a confidentializing process has been completed, and thereby it is possible to identify a location of an interruption easily and to restart the confidentializing process at an early stage.

In a confidentializing process in mode M1, the personal information 664-*i* is transferred to the backup storage device 631-*i* at a different timing for each hospital. Thus, it is not always that the latest personal information 664-*i* of each hospital has been collected at a moment when a confidentializing process has started in mode M2.

In response to this, the analysis system 613 transmits an update-to-latest request that instructs the server 623-*i* of each hospital to update the backup DB 653-*i* to the latest version. Then, the server 623-*i* instructs the operation storage device 624-*i* to make a backup when the personal information 664-*i* in the backup DB 653-*i* is not the latest version and a backup of the personal information 664-*i* can be made instantaneously. Thereby, it is possible to collect the latest personal information 664-*i* from all the hospitals as much as possible without causing troubles to operations of the hospitals in a confidentializing process in mode M2.

Next, explanations will be given to an operation sequence in mode M1 while referring to FIG. 19 through FIG. 21.

Figure 19:
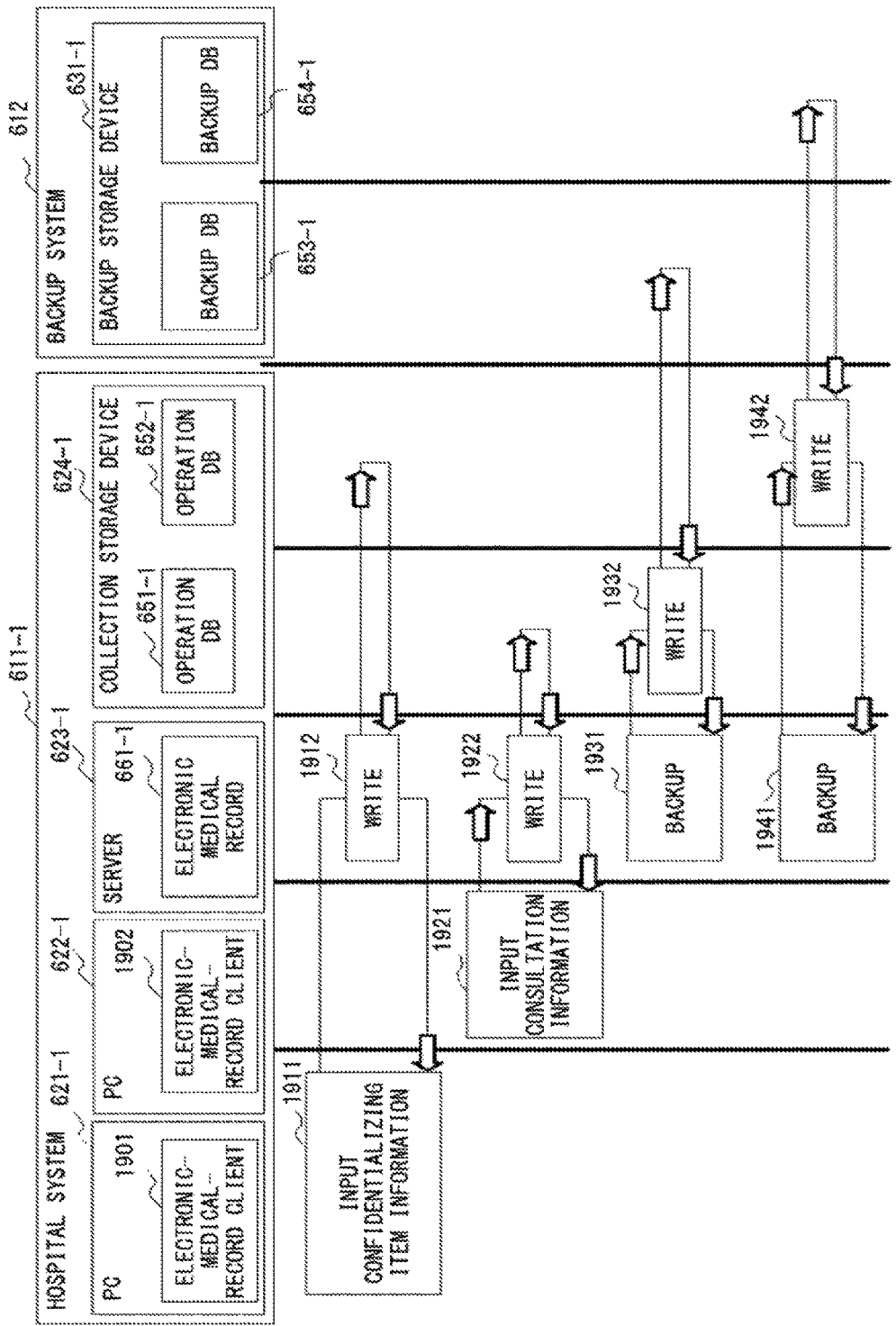
FIG. 19 illustrates an information provision sequence in mode M1.

FIG. 19 illustrates an example of an information provision sequence in mode M1. An electronic-medical-record client 1901 and an electronic-medical-record client 1902, which are applications, are installed in the PCs 621-1 and 622-1 in hospital A.

First, in accordance with manipulation made by a staff member or a patient of hospital A, the electronic-medical-record client 1901 inputs confidentializing item information specified by a patient to the electronic medical record 661-1 in the server 623-1 (step 1911). Then, the server 623-1 writes the confidentializing item information received by the electronic medical record 661-1 to the operation DB 652-1 of the operation storage device 624-1 as the confidentializing item information 663-1 (step 1912).

Next, the electronic-medical-record client 1902 inputs consultation information of that patient to the electronic medical record 661-1 in accordance with manipulation made by a doctor of hospital A (step 1911). Also, the server 623-1 writes the consultation information received by the electronic medical record 661-1 to the operation DB 651-1 of the operation storage device 624-1 as the personal information 662-1 (step 1922).

Thereafter, a system administrator of each hospital makes a backup periodically. Then, the server 623-1 transmits a backup instruction of the personal information 662-1 to the operation storage device 624-1 (step 1931). Thereafter, the operation storage device 624-1 writes a copy of the personal information 662-1 to the backup DB 653-1 of the backup storage device 631-1 as the personal information 664-1 (step 1932).

Next, the server 623-1 transmits a backup instruction of the confidentializing item information 663-1 to the operation storage device 624-1 (step 1941). Then, the operation storage device 624-1 writes a copy of the confidentializing item information 663-1 to the backup DB 654-1 of the backup storage device 631-1 as the confidentializing item information 665-1 (step 1942).

In hospital B as well, an information provision sequence that is similar to that in FIG. 19 writes the personal information 662-2 and the confidentializing item information 663-2 to the operation storage device 624-2. Then, the personal information 664-2 and the confidentializing item information 665-2 are written to the backup storage device 631-2.

Figure 20A:
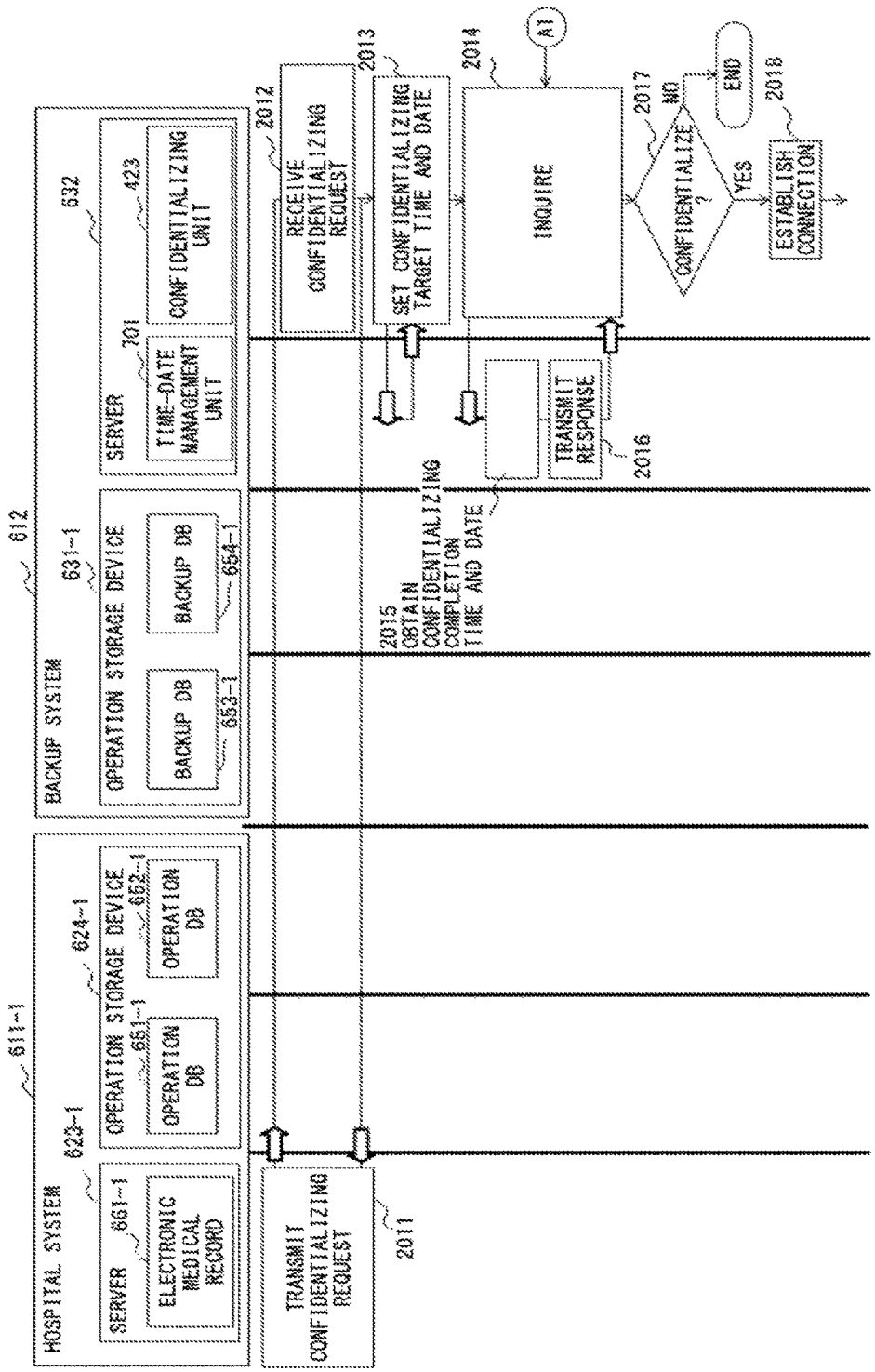
FIG. 20A illustrates an information-confidentializing sequence in mode M1 (first part)
Figure 20B:
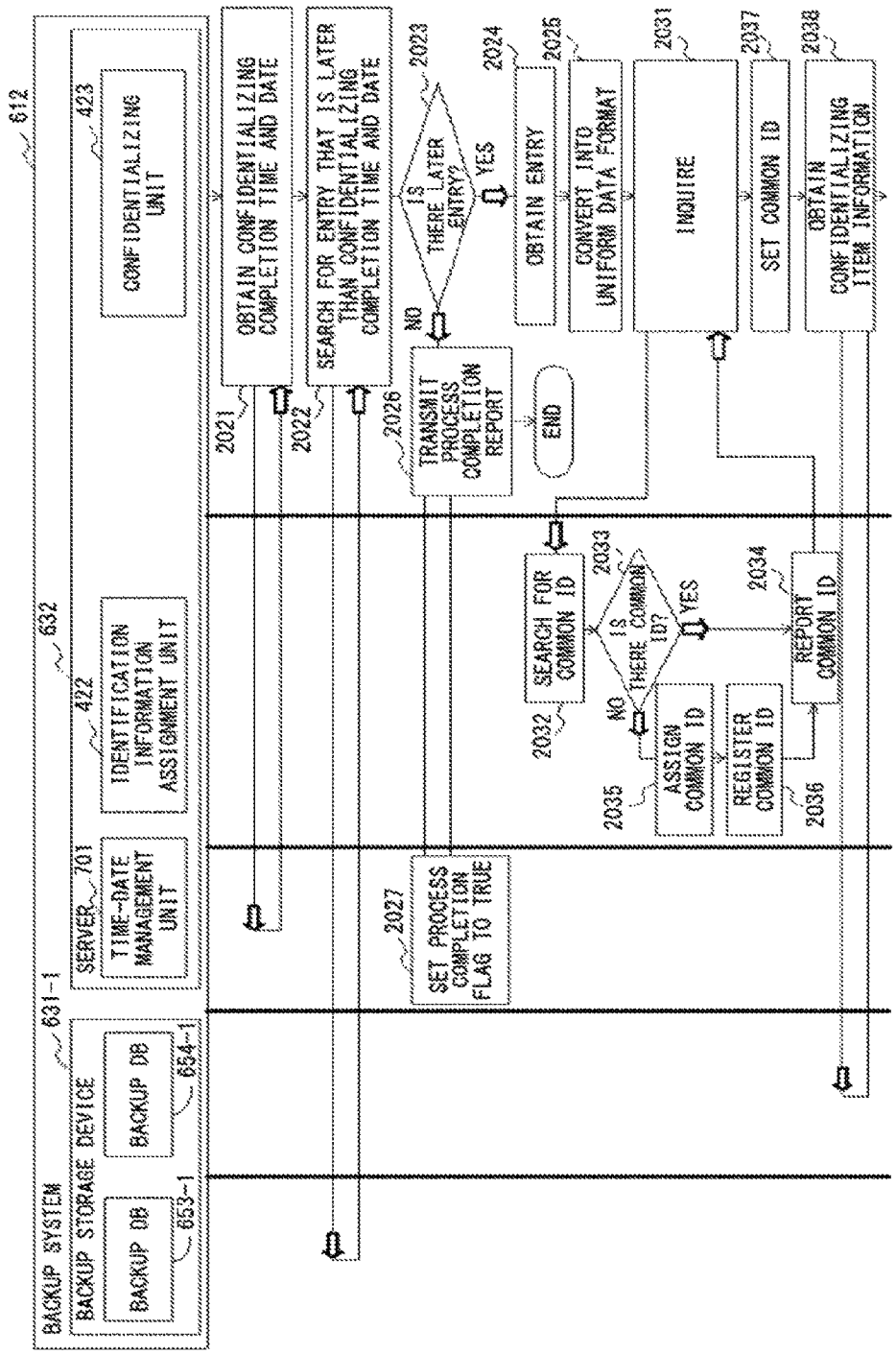
FIG. 20B illustrates an information-confidentializing sequence in mode M1 (second part)
Figure 20C:
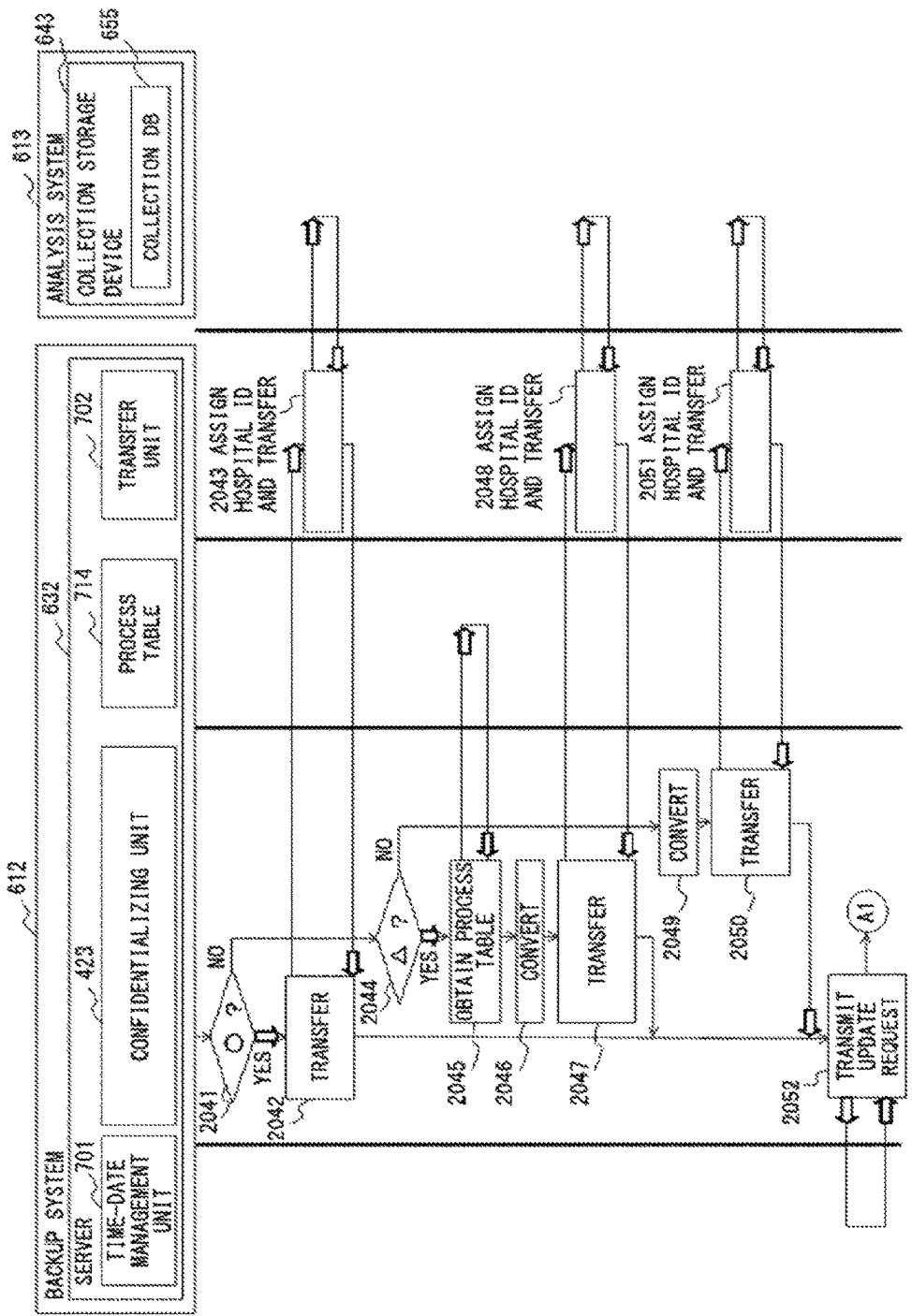
FIG. 20C illustrates an information-confidentializing sequence in mode M1 (third part)

FIG. 20A through FIG. 20C illustrate an example of an information confidentializing sequence in mode M1. First, the server 623-1 in hospital A transmits a confidentializing request including a confidentializing target time and date to the server 632 of the backup system 612 (step 2011). As the confidentializing target time and date included in the confidentializing request, for example a time and date that is later than the times and dates of update of the entries included in the personal information 664-1 may be set. The confidentializing unit 423 of the server 632 receives a confidentializing request and accepts that confidentializing request (step 2012).

Next, the confidentializing unit 423 instructs the time-date management unit 701 to set a confidentializing target time and date included in the confidentializing request (step 2013). The time-date management unit 701 sets the specified confidentializing target time and date to a confidentializing target time and date corresponding to the hospital ID of hospital A on the time-date table 712, and sets a process completion flag corresponding to that confidentializing target time and date to "false". The confidentializing unit 423 inquires of the time-date management unit 701 about whether or not to perform a confidentializing process (step 2014).

The time-date management unit 701 obtains a confidentializing completion time and date and a confidentializing target time and date corresponding to the hospital ID of hospital A from the time-date table 712 (step 2015). Then, the time-date management unit 701 compares the confidentializing completion time and date and the confidentializing target time and date so as to transmit, to the confidentializing unit 423, whether or not to perform a confidentializing process (step 2016). When the confidentializing target time and date is later than the confidentializing completion time and date, the time-date management unit 701 determines to perform a confidentializing process, and when the confidentializing target time and date is equal to or earlier than the confidentializing completion time and date, the time-date management unit 701 determines to not perform a confidentializing process.

Next, the confidentializing unit 423 checks the response received from the time-date management unit 701 (step 2017), and establishes a connection to the backup storage device 631-1 (step 2018) when a confidentializing process is to be performed (YES in step 2017). When a confidentializing process is not to be performed (NO in step 2017), the confidentializing unit 423 terminates the process.

Next, the confidentializing unit 423 obtains the confidentializing completion time and date corresponding to the hospital ID of hospital A from the time-date table 712 via the time-date management unit 701 (step 2021). Then, the confidentializing unit 423 searches the personal information 664-1 of the backup DB 653-1 for an entry having a time and date of update that is later than the confidentializing completion time and date (step 2022) so as to check whether or not there is such an entry (step 2023).

When there is an entry that is later than the confidentializing completion time and date (YES in step 2023), the confidentializing unit 423 obtains that entry from the personal information 664-1 (step 2024). Then, the confidentializing unit 423 uses a conversion program of hospital A so as to convert the data format of the obtained entry into the uniform data format (step 2025).

When there is not an entry that is later than the confidentializing completion time and date (NO in step 2023), the confidentializing unit 423 transmits a process completion report to the time-date management unit 701 (step 2026) so as to terminate the process. Then, the time-date management unit 701 sets a process completion flag corresponding to the hospital ID of hospital A to "true" on the time-date table 712 (step 2027).

After performing the process in step 2025, the confidentializing unit 423 uses a personal ID included in the obtained entry so as to inquire of the identification information assignment unit 422 of a common ID that corresponds to the personal ID (step 2031).

The identification information assignment unit 422 searches the ID table 711 for a common ID that corresponds to the personal ID (step 2032), and checks whether or not there exits that common ID (step 2033). When there is a common ID that corresponds to the personal ID (YES in step 2033), the identification information assignment unit 422 reports that common ID to the confidentializing unit 423 (step 2034).

When there is not a common ID that corresponds to the personal ID (NO in step 2033), the identification information assignment unit 422 assigns a new common ID to that personal ID (step 2035). Then, the identification information assignment unit 422 registers, in the ID table 711, a correspondence relationship between that personal ID and the assigned common ID (step 2036), and reports the assigned common ID to the confidentializing unit 423 (step 2034).

Next, the confidentializing unit 423 sets the common ID reported from the identification information assignment unit 422 in the obtained entry (step 2037). Then, the confidentializing unit 423 obtains the confidentializing item information 655-1 of the patient corresponding to the obtained entry from the backup DB 654-1 (step 2038), and checks whether or not the symbol is "○" for each item (step 2041).

When the symbol is "○", (YES in step 2041), the confidentializing unit 423 transfers the information of that item included in the entry to the transfer unit 702 as it is (step 2042). Then, the transfer unit 702 assigns a hospital ID to the received information and transfers the information to the collection storage device 643 of the analysis system 613 (step 2043). When the symbol is not "○" (NO in step 2041), the confidentializing unit 423 checks whether or not the symbol is "Δ" (step 2044).

When the symbol is "Δ" (YES in step 2044), the confidentializing unit 423 obtains the process table 714 (step 2045), and uses the process table 714 to convert the information of that item included in the entry into simplified information (step 2046). Then, the confidentializing unit 423 transfers the converted information to the transfer unit 702 (step 2047), and the transfer unit 702 assigns the hospital ID to the received information so as to transfer the information to the collection storage device 643 (step 2048).

When the symbol is not "Δ", (NO in step 2044), the confidentializing unit 423 converts the information of that item included in the entry into data indicating that information has been confidentialized (step 2049). Then, the confidentializing unit 423 transfers the converted information to the transfer unit 702 (step 2050), and the transfer unit 702 assigns the hospital ID to the received information so as to transfer the information to the collection storage device 643 (step 2051).

The collection storage device 643 stores information and hospital IDs of respective items received from the transfer unit 702 so as to store them in the collection DB 655 as entries of the confidentialized personal information 666 that corresponds to the personal information 664-1.

Next, the confidentializing unit 423 transmits an update request of the time-date table 712 to the time-date management unit 701 (step 2052). Then, from among times and dates of update in the entries that have been transferred completely, the time-date management unit 701 sets the latest time and date of update as the confidentializing completion time and date that corresponds to the hospital ID of the hospital A on the time-date table 712. When there are a plurality of entries having the latest time and date of update, the time-date management unit 701 sets the number representing the order of the entry in which the transfer has been completed as an equal-time sequential number that corresponds to the set confidentializing completion time and date.

Next, the confidentializing unit 423 repeats the processes in and after step 2014. When receiving a response indicating that a confidentializing process is not to be performed (NO in step 2017) or when an entry that is later than the confidentializing completion time and date does not exist (NO in step 2023), the confidentializing unit 423 terminates the process.

An information confidentializing sequence similar to that in FIG. 20A through FIG. 20C performs a confidentializing process also on the personal information 664-2 of hospital B, and the personal information 664-2 that has been confidentialized is added to the confidentialized personal information 666.

Figure 21:
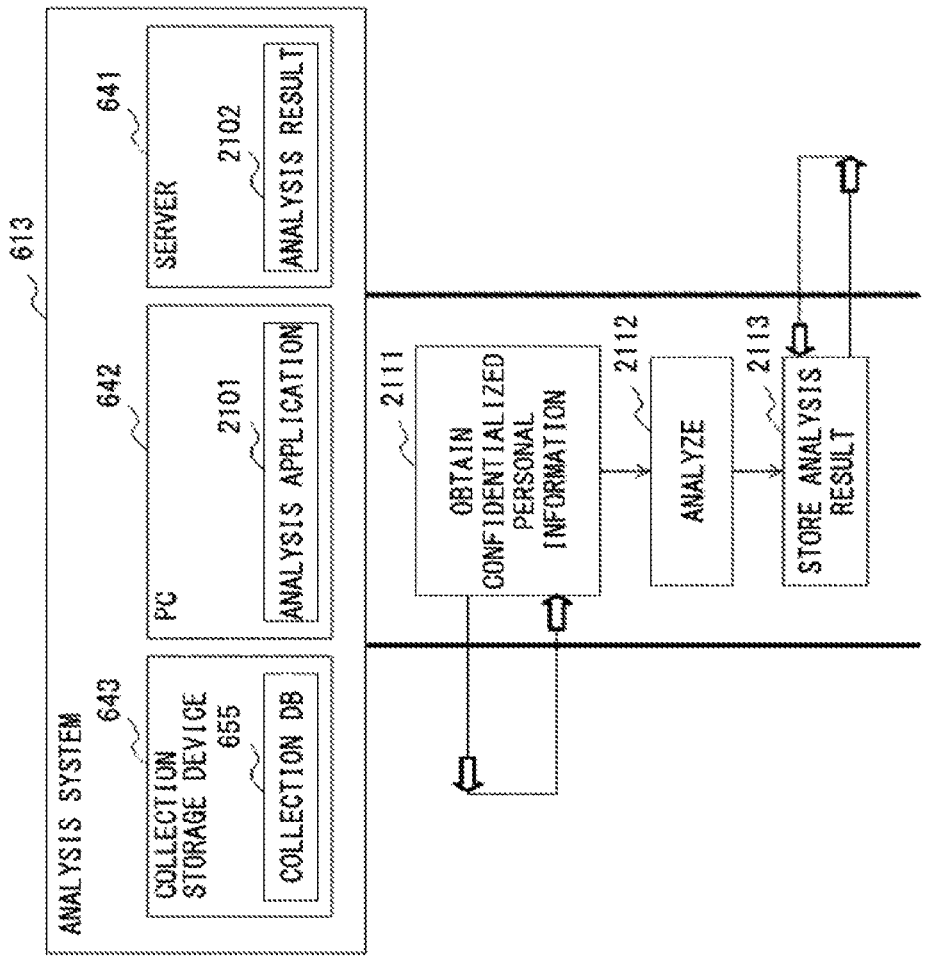
FIG. 21 illustrates an information analysis sequence in mode M1.

FIG. 21 illustrates an example of an analysis sequence in mode M1. The PC 642 of the analysis system 613 has an analysis application 2101 installed in it. First, in accordance with manipulation made by an analyzer of an information analysis institution, the analysis application 2101 obtains the confidentialized personal information 666 from the collection DB 655 of the collection storage device 643 (step 2111). Next, in accordance with manipulation made by the analyzer, the analysis application 2101 analyzes the confidentialized personal information 666 (step 2112), and stores an analysis result 2102 in the server 641 (step 2113).

Figure 22A:
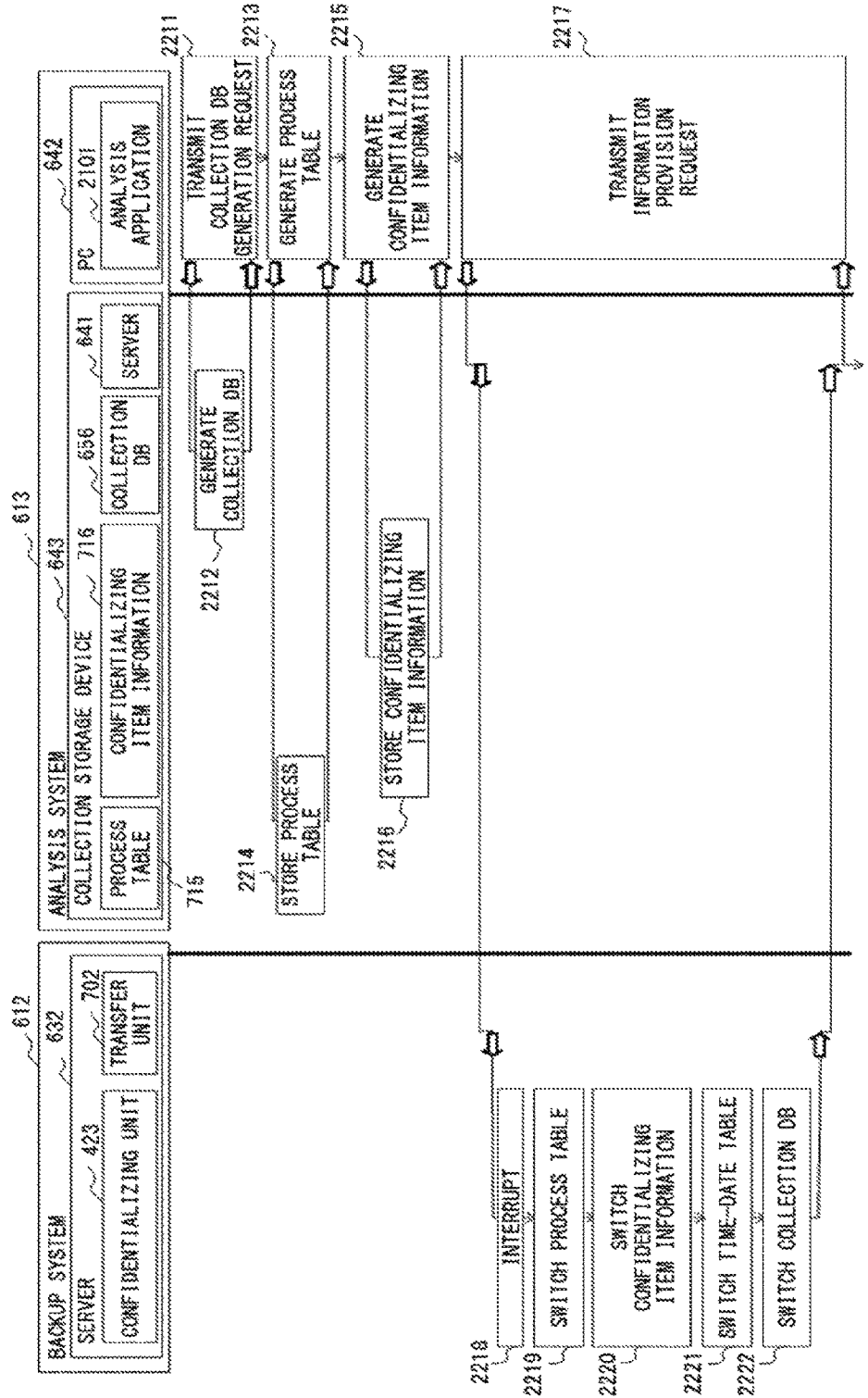
FIG. 22A illustrates an operation sequence in mode M2 (first part)
Figure 22B:
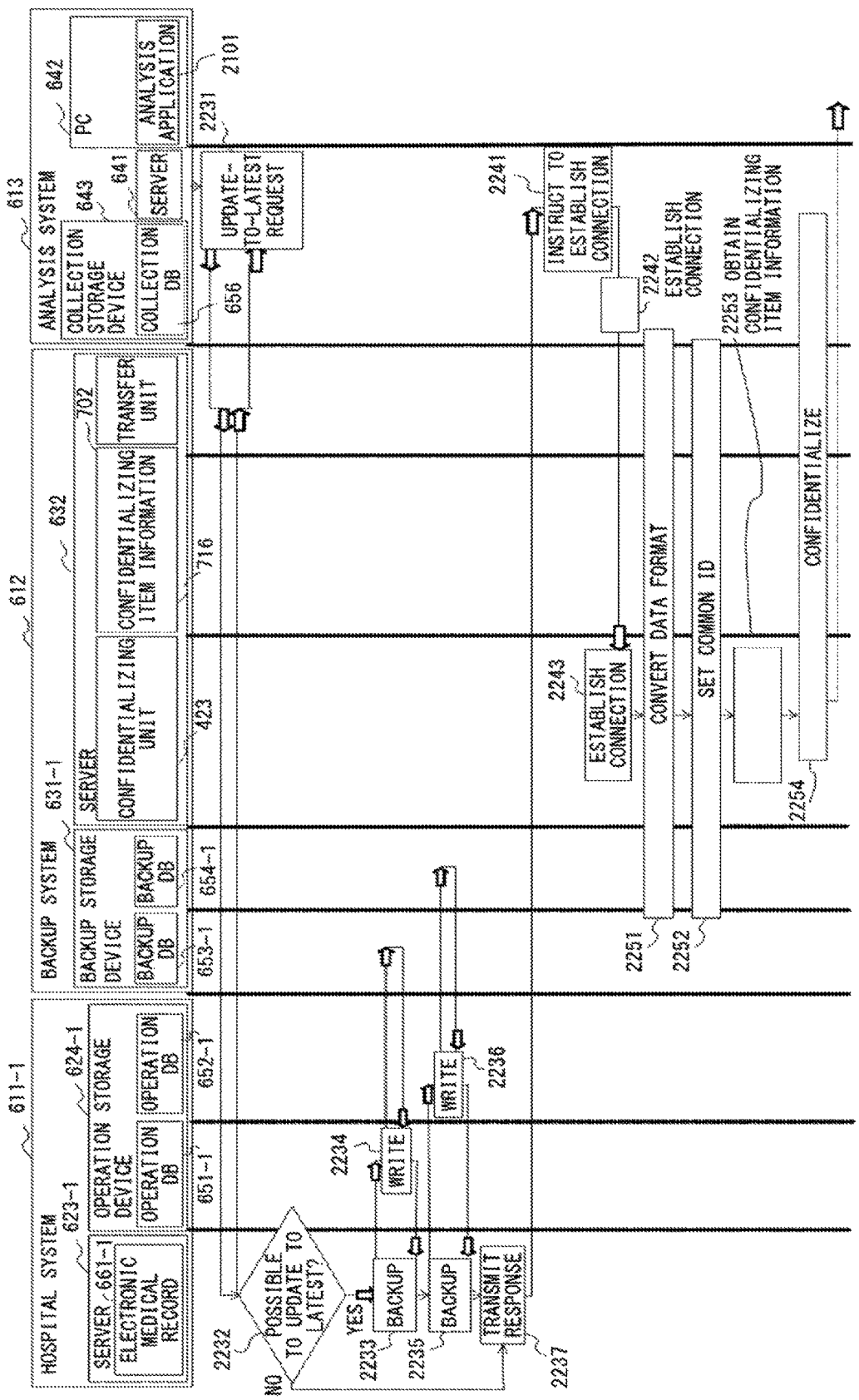
FIG. 22B illustrates an operation sequence in mode M2 (second part)
Figure 22C:
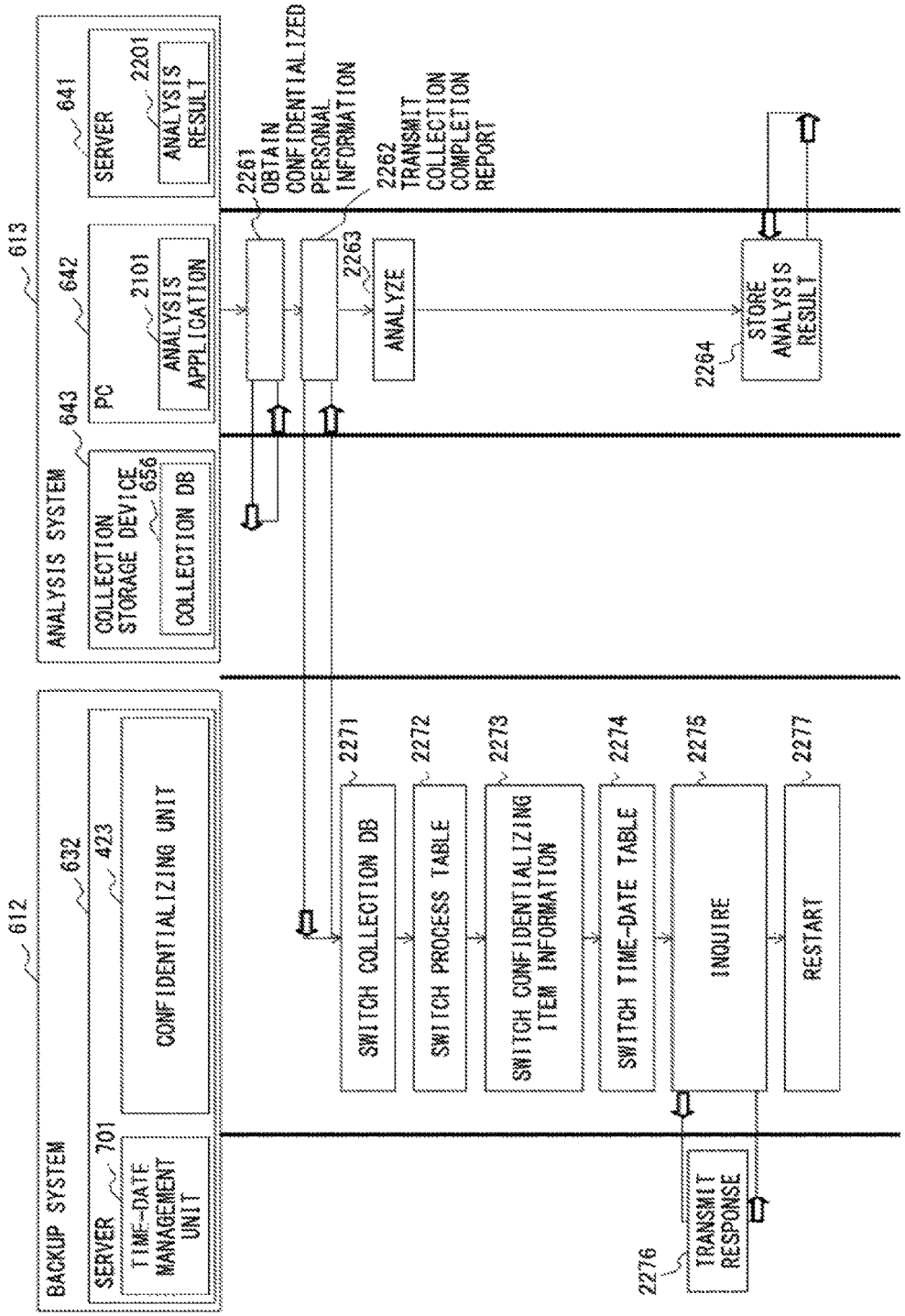
FIG. 22C illustrates an operation sequence in mode M2 (third part)

FIG. 22A through FIG. 22C illustrate an example of an operation sequence in mode M2. First, in accordance with manipulation made by the analyzer of the information analysis institution, the analysis application 2101 of the analysis system 613 transmits a collection DB generation request to the collection storage device 643 (step 2211). The collection storage device 643 generates the collection DB 656 (step 2212).

Next, the analysis application 2101 generates the process table 715 in accordance with manipulation made by the analyzer, and transmits the table to the collection storage device 643 (step 2213). The collection storage device 643 stores the received process table 715 (step 2214).

Next, in accordance with manipulation made by the analyzer, the analysis application 2101 generates the confidentializing item information 716 so as to transmit the information to the collection storage device 643 (step 2215). The collection storage device 643 stores the received confidentializing item information 716 (step 2216).

Next, in accordance with manipulation made by the analyzer, the analysis application 2101 transmits an information provision request including a collection period to the server 632 of the backup system 612 together with the process table 715 and the confidentializing item information 716 (step 2217).

The confidentializing unit 423 of the server 632 interrupts a confidentializing process for each hospital in mode M1 (step 2218), and switches from the process table 714 to the process table 715 (step 2219) as a process table that is referred to in a confidentializing process (step 2219). Next, the confidentializing unit 423 switches from the confidentializing item information 665-*i* to the confidentializing item information 716 as a confidentializing item information that is to be referred to in a confidentializing process (step 2220).

Next, the confidentializing unit 423 switches from the time-date table 712 to the time-date table 713 as a date table that is to be referred to in a confidentializing process (step 2221). Upon this, the time-date management unit 701 sets a time and date that is earlier than the collection starting time and date of the collection period included in an information provision request as a confidentializing completion time and date for each hospital on the time-date table 713, and sets a collection ending time and date as a confidentializing target time and date for each hospital. Then, the time-date management unit 701 sets the process completion flag of each hospital to "false".

Next, the confidentializing unit 423 switches from the collection DB 655 to the collection DB 656 as a transfer destination for confidentialized personal information (step 2222).

Next, the server 641 of the analysis system 613 transmits an update-to-latest request of the backup DB 653-1 to the backup system 612 (step 2231), and the transfer unit 702 transfers the update-to-latest request to the hospital system 611-1 of the hospital A.

The server 623-1 of the hospital system 611-1 determines whether or not it is possible to update the backup DB 653-1 to the latest version (step 2232). The server 623-*i* determines that it is possible to perform updating to the latest version when the personal information 664-*i* in the backup DB 653-1 is not the latest version and a backup of the personal information 664-1 can be made instantaneously. Also, the server 623-1 determines that it is not possible to perform updating to the latest version when the personal information 664-1 of the backup DB 653-1 is the latest version or when it is not possible to make a backup of the personal information 664-1 instantaneously.

When it is possible to perform updating to the latest version (YES in step 2232), the server 623-1 transmits a backup instruction of the personal information 662-1 to the operation storage device 624-1 (step 2233). Then, the operation storage device 624-1 writes a copy of the personal information 662-1 to the backup DB 653-1 of the backup storage device 631-1 as the personal information 664-1 (step 2234).

Next, the server 623-1 transmits a backup instruction of the confidentializing item information 663-1 to the operation storage device 624-1 (step 2235). Then, the operation storage device 624-1 writes a copy of the confidentializing item information 663-1 to the backup DB 654-1 of the backup storage device 631-1 as the confidentializing item information 665-1 (step 2236).

Then, the server 623-1 transmits, to the server 641, a response indicating the completion of updating to the latest version (step 2237). When updating to the latest version is not possible (NO in step 2232), the server 623-1 immediately transmits a response indicating completion of updating to the latest version to the server 641 (step 2237).

Next, the server 641 instructs the collection storage device 643 and the server 632 to establish a connection between the collection DB 656 and the confidentializing unit 423 (step 2241). Then, the collection storage device 643 establishes a connection between the collection DB 656 and the confidentializing unit 423 (step 2242) and the server 632 also establishes a connection between the collection DB 656 and the confidentializing unit 423 (step 2243).

Next, the confidentializing unit 423 performs a data format conversion process (step 2251), performs a common ID setting process (step 2252), obtains the confidentializing item information 716 (step 2253), and performs a confidentializing process (step 2254).

Processes similar to those from step 2014 of FIG. 20A through step 2027 of FIG. 20B are performed in step 2251, while processes similar to those in step 2031 through step 2037 of FIG. 20B are performed in step 2252. Also, processes similar to those in step 2041 through 2052 of FIG. 20C are performed in step 2254, and processes in and after step 2014 are repeated after the process in step 2052. Thereby, the personal information 664-1 that has been confidentialized is stored in the collection DB 656 as the confidentialized personal information 667.

When a confidentializing process is terminated for the entries corresponding to the collection period, the confidentializing unit 423 reports the completion of a confidentializing process for the personal information 664-1 of hospital A to the PC 642 of the analysis system 613.

An operation sequence similar to that of FIG. 22B performs a confidentializing process also on the personal information 664-2 of hospital B, and the personal information 664-2 that has been confidentialized is added to the confidentialized personal information 667.

Upon completion of confidentializing processes for the personal information 664-i of all hospitals, the analysis application 2101 obtains the confidentialized personal information 667 from the collection DB 656 of the collection storage device 643 in accordance with manipulation made by the analyzer (step 2261), and transmits a collection completion report to the server 632 (step 2262). Next, in accordance with manipulation made by the analyzer, the analysis application 2101 analyzes the confidentialized personal information 667 (step 2263) so as to store the analysis result 2201 to the server 641 (step 2264).

The confidentializing unit 423 that received the collection completion report switches from the collection DB 656 to the collection DB 655, which had been used until the previous switching, as a transfer destination for the confidentialized personal information (step 2271). Next, the confidentializing unit 423 switches from the process table 715 to the process table 714, which had been used until the previous switching, as a process table that is to be referred to in a confidentializing process (step 2272).

Next, the confidentializing unit 423 switches from the confidentializing item information 716 to the confidentializing item information 665-i, which had been used until the previous switching, as confidentializing item information that is to be referred to in a confidentializing process (step 2273). Next, the confidentializing unit 423 switches from the time-date table 713 to the time-date table 712, which had been used until the previous switching, as a data table that is to be referred to in a confidentializing process (step 2274).

Next, the confidentializing unit 423 inquires of the time-date management unit 701 about the location of the interruption in the confidentializing process in mode M1 (step 2275). The time-date management unit 701 refers to the time-date table 712 so as to search for an entry having a process completion flag set to "false". Then, the time-date management unit 701 transmits, to the confidentializing unit 423, a response including the hospital ID, the confidentializing completion time and date and the equal-time sequential number of that entry (step 2276).

A hospital having a process completion flag set to "false" corresponds to a hospital for which a confidentializing process was interrupted in mode M1, and the confidentializing completion time and date and the equal-time sequential number represent a location of an interruption in the personal information 664-i of that hospital.

From among pieces of the personal information 664-i of a hospital specified by a hospital ID included in the response, the confidentializing unit 423 restarts a confidentializing process in mode M1 for an entry having a time and date of update equal to or later than the confidentializing completion time and date included in the response (step 2277). In such a case, the processes in and after step 2021 of FIG. 20B are restarted.

When there are a plurality of entries having the same time and date of update as the confidentializing completion time and date, the confidentializing process is restarted from the entry subsequent to the order specified by the equal-time sequential number. When there is only one entry having the same time and date of update as the confidentializing completion time and date, the confidentializing process is restarted from the entry having the next time and date of update.

Incidentally, the ID table 711, the time-date table 712, the time-date table 713, the process table 714, the process table 715 and the confidentializing item information 716 are common resources in the information processing system 601 illustrated in FIG. 6. In modes M1 and M2, the server 632 performs a confidentializing process on the personal information 664-i of a plurality of hospitals while accessing these common resources.

When an operation is performed in mode M2 in accordance with an urgent request from the information analysis institution particularly, the server 632 is to perform confidentializing processes for pieces of the personal information 664-i of a plurality of hospitals in parallel while accessing common resources. There may be no problem when the number of process target hospitals is small, whereas a large number of such hospitals may lead to a possibility that accesses will concentrate on the common resources, delaying the processes.

In order to cope with this problem, it may be possible to arrange virtual machines (VMs) on a plurality of physical servers or a cloud for performing confidentializing processes of respective hospitals. In such a case, the common resources except the ID table 711 do not need to synchronize with each other over a plurality of hospitals, making it possible to arrange the time-date tables 712, the time-date tables 713, the process tables 714, the process tables 715 and the confidentializing item information 716 in the VMs of the respective hospitals. Meanwhile, the information of the ID table 711 is arranged in a physical server that is independent from the VMs because it is desirable for the information of the ID table 711 to synchronize between the hospitals.

Figure 23:
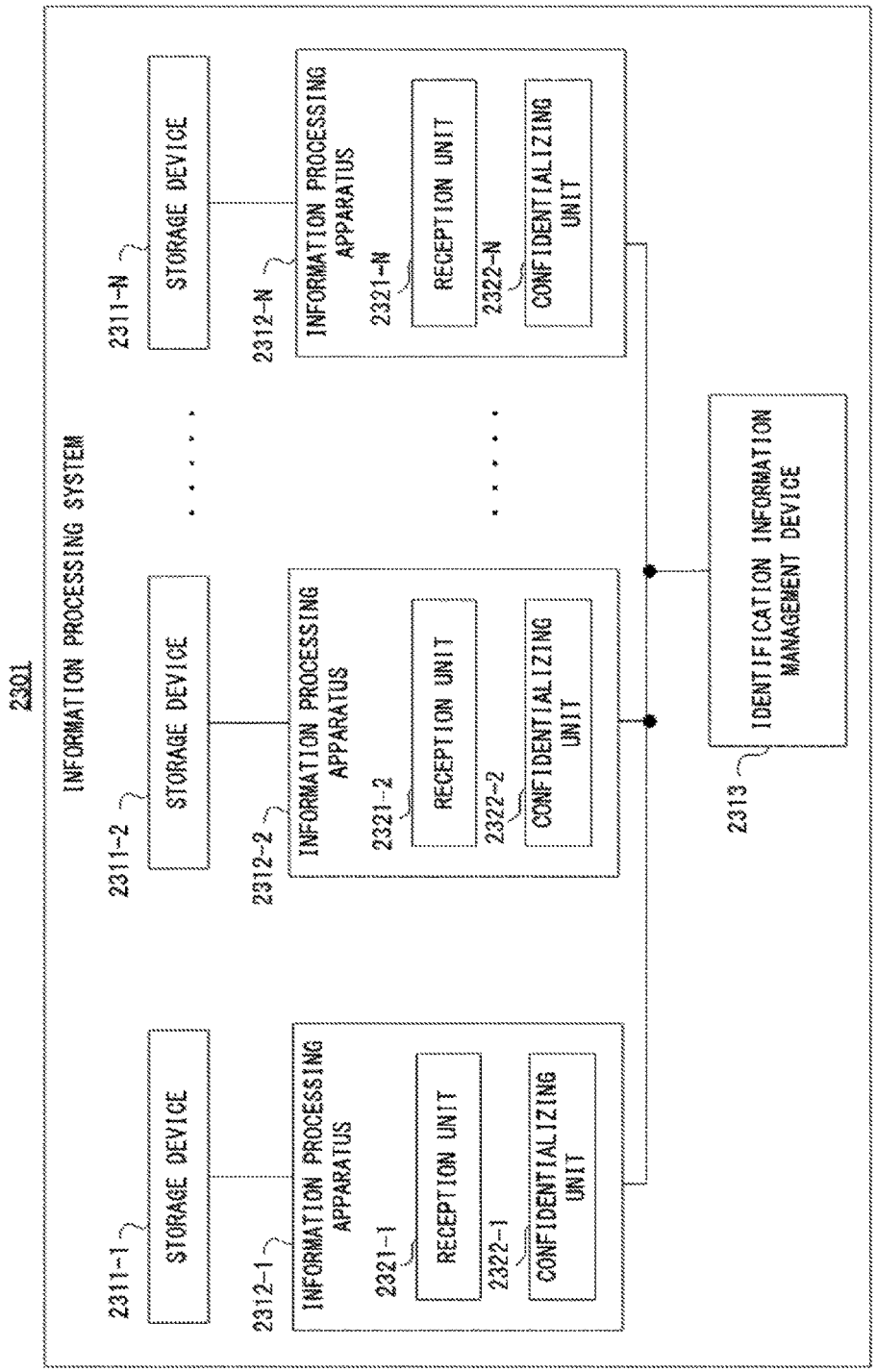
FIG. 23 illustrates a configuration of a second information processing system.

FIG. 23 illustrates a configuration example of a second information processing system as described above. An information processing system 2301 illustrated in FIG. 23 includes storage devices 2311-1 through 2311-N (N is an integer equal to or greater than two), information processing apparatuses 2312-1 through 2312-N and an identification information management device 2313. Each of the information processing apparatuses 2312-*j* (j=1 through N) includes a reception unit 2321-*j* and a confidentializing unit 2322-*j*.

The storage devices 2311-1 through 2311-N store personal information transferred from N operation databases respectively of the N information provision institutions. The information processing apparatus 2321-*j* of the information processing apparatus 2312-*j* receives, from the identification information management device 2313, common identification information shared between a plurality of information provision institutions for identifying a person. The confidentializing unit 2322-*j* uses the common identification information for performing a confidentializing process.

Figure 24:
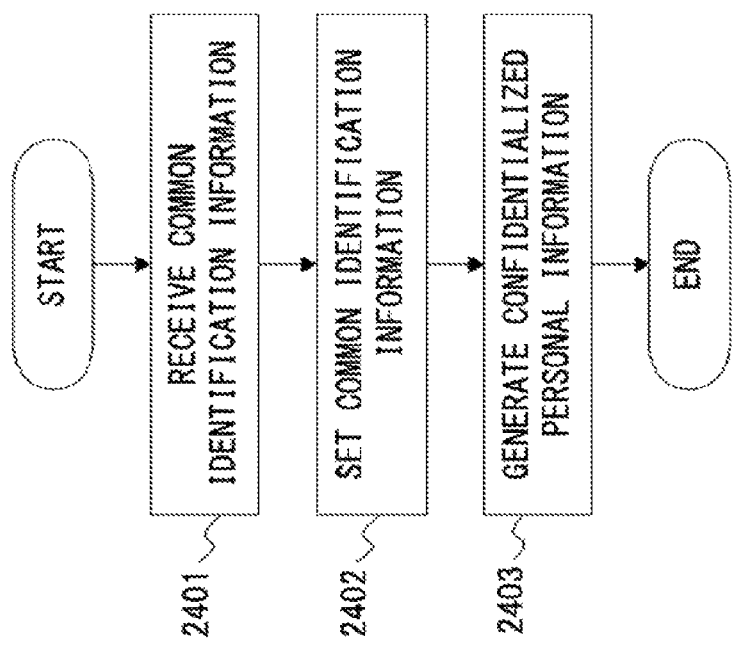
FIG. 24 is a flowchart illustrating a second confidentializing process.

FIG. 24 is a flowchart illustrating an example of a second confidentializing process performed by the information processing apparatus 2312-*j* illustrated in FIG. 23. First, the reception unit 2321-*j* receives, from the identification information management device 2313, common identification information that is shared between N information provision institutions for identifying a person (step 2401).

Next, the confidentializing unit 2322-*j* sets the received common identification information for personal information that is transferred to the storage device 2311-*j* from the operation database of the j-th information provision institution (step 2402). Then, the confidentializing unit 2322-*j* confidentializes the personal information for which the common identification information has been set, and thereby generates confidentialized personal information (step 2403).

The information processing system 2301 as described above makes it possible to identify pieces of information of the same person from among pieces of confidentialized personal information obtained by confidentializing pieces of personal information collected from a plurality of information provision institutions.

FIG. 25 illustrates a specific example of the information processing system 2301 illustrated in FIG. 23. An information processing system 2501 illustrated in FIG. 25 includes hospital systems 2511-1 through 2511-M (M is an integer equal to or greater than N), a backup system 2512 and an analysis system 2513.

The hospital system 2511-*i* (i=1 through M) is the hospital system of the i-th hospital, and has a similar configuration to that of the hospital system 611-*i* illustrated in FIG. 6.

The backup system 2512 includes backup storage devices 2521-1 through 2521-M, servers 2522-1 through 2522-N and a server 2523. The backup storage device 2521-*i* corresponds to the storage device 2311-*i* illustrated in FIG. 23, the server 2522-*j* corresponds to the information processing apparatus 2312-*j*, and the server 2523 corresponds to the identification information management device 2313.

The backup storage device 2521-*i* has a similar configuration to that of the backup storage device 631-*i* illustrated in FIG. 6.

In each server 2522-*j*, a VM of at least one hospital operates. In this example, VMs 2524-1 through 2524-3 respectively of the first through third hospitals operate in the server 2522-1. The VMs 2524-4 and 2524-5 respectively of the fourth and fifth hospitals operate in the server 2522-2, and VMs 2524-(M−1) and 2524-M respectively of the (M−1)-th and M-th hospitals operate in the server 2522-N.

The server 2523 includes an identification information assignment unit 2525, and stores an ID table 2526. The ID table 2526 corresponds to the ID table 711 illustrated in FIG. 7.

The analysis system 2513 includes a server 2531, a PC 2532 and a collection storage device 2533. The collection storage device 2533 has a similar configuration to that of the collection storage device 643 illustrated in FIG. 6. With an increase in the number of hospitals, scale-out may be performed for the collection storage device 2533.

Figure 26:
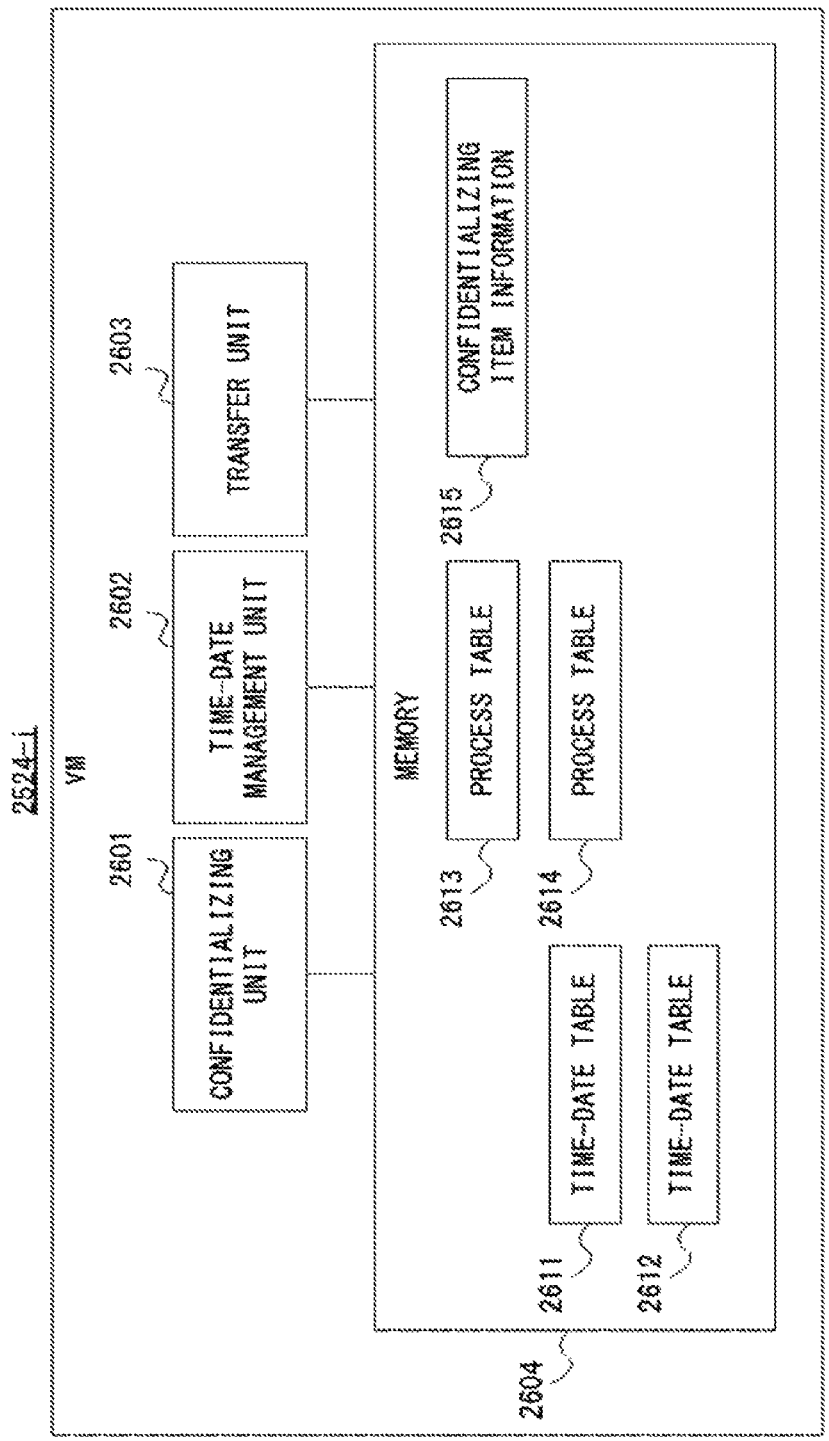
FIG. 26 illustrates a functional configuration of a VM.

FIG. 26 illustrates a functional configuration example of the VM 2524-*i* illustrated in FIG. 25. The VM 2524-*i* illustrated in FIG. 26 includes a confidentializing unit 2601, a time-date management unit 2602, a transfer unit 2603 and a memory 2604. The confidentializing unit 2601 is an application that is executed by the VM 2524-*i*, and provides similar functions to those provided by the confidentializing unit 423 of FIG. 7 and the confidentializing unit 2322-*i* of FIG. 23. The time-date management unit 2602 and the transfer unit 2603 are also applications that are executed by the VM 2524-*i*, and provide similar functions to those provided by the time-date management unit 701 and the transfer unit 702 of FIG. 7.

The memory 2604 corresponds to a storage area in a storage unit of the server 2522-*j*, and stores time-date tables 2611 and 2612, the process tables 2613 and 2614 and the confidentializing item information 2615.

The time-date tables 2611 and 2612 correspond to the time-date tables 712 and 713 illustrated in FIG. 7, respectively. However, the time-date tables 2611 and 2612 include only entries for a confidentializing process for the personal information 664-*i* of the i-th hospital, differently from the time-date tables 712 and 713.

FIG. 27 illustrates an example of the time-date table 2611 illustrated in FIG. 26. In this example, the time-date table 2611 includes only an entry of a hospital ID of "100" from among the entries on the time-date table 712 illustrated in FIG. 13. The time-date table 2612 is also similar to the time-date table 2611.

The process tables 2613 and 2614 and the confidentializing item information 2615 respectively correspond to the process tables 714 and 715 and the confidentializing item information 716 illustrated in FIG. 7.

Similarly to the information processing system 601 illustrated in FIG. 6, the information processing system 2501 illustrated in FIG. 25 can perform an operation in mode M1, in which a confidentializing process is performed in accordance with a request from each hospital, and an operation in mode M2, in which a confidentializing process is performed in accordance with a request from an information analysis institution.

In the above, the hospital system 2511-*i* operates similarly to the hospital system 611-*i* illustrated in FIG. 6, and the backup storage device 2521-*i* of the backup system 2512 operates similarly to the backup storage device 631-*i*.

The confidentializing unit 2601, the time-date management unit 2602 and the transfer unit 2603 of the VM 2524-*i* provide similar functions to those provided by the confidentializing unit 423, the time-date management unit 701 and the transfer unit 702 illustrated in FIG. 7. The identification information assignment unit 2525 of the server 2523 operates similarly to the identification information assignment unit 422.

The server 2531, the PC 2532 and the collection storage device 2533 of the analysis system 2513 operate similarly to the server 641, the PC 642 and the collection storage device 643 illustrated in FIG. 6.

The operation sequence in mode M1 is similar to that illustrated in FIG. 19 through FIG. 21, and the operation sequence in mode M2 is similar to that illustrated in FIG. 22A through FIG. 22C. However, the confidentializing unit 2601 and the time-date management unit 2602 of each VM 2524-*i* perform a process by using the time-date table 2611 and the process table 2613 stored in the memory 2604 in the operation sequence illustrated in FIG. 20A through FIG.

20C. Also, when referring to or updating the ID table 2526, the confidentializing unit 2601 accesses the server 2523 so as to make a request for the assignment unit 2525 to perform a process.

Similarly, the confidentializing unit 2601 and the time-date management unit 2602 of each VM 2524-i perform a process by using the time-date table 2612 and the process table 2614 stored in the memory 2604 in the operation sequence illustrated in FIG. 22A through FIG. 22C. Also, when referring to or updating the ID table 2526, the confidentializing unit 2601 accesses the server 2523 so as to make a request for the assignment unit 2525 to perform a process.

According to the information processing system 2501 of FIG. 25, a confidentializing process is performed by using an independent resource that is held by the VM 2524-i of each hospital, leading to a situation where confidentializing processes for a plurality of hospitals are executed in parallel without delay even when there are many hospitals as process target.

It is also possible to use passwords to protect the personal information 664-i that is processed by the VM 2524-i of each hospital. In such a case, even when a malicious person obtains a password and accesses one of the VMs 2524-i in the backup system 2512, accesses to the other VMs 2524-i by using the same password are blocked. This results in higher security than the information processing system 601 illustrated in FIG. 6.

Note that the information processing apparatuses of the hospitals may be virtualized by using a container etc. instead of the VMs 2524-i. Virtualization using containers can further increase the speed of confidentializing processes.

In the information processing system 601 illustrated in FIG. 6 and the information processing system 2501 illustrated in FIG. 25, an information provision institution may be an institution that is not a hospital that provides patients' consultation information. Examples of an information provision institution may include a store that provides customers' purchase information, an educational institution such as a school, a cram school, etc. that provide students' grade information, a financial institution such as a bank that provides customers' balances, records of transactions, etc.

When a store serves as an information provision institution, pieces of customers' purchase information are collected as pieces of personal information, and analysis results representing preferences of the customers are provided to information users such as a restaurant etc. When an educational institution serves as an information provision institution, pieces of students' grade information are collected, and analysis results representing tendencies etc. for each subject are provided to information users such as a education material publisher company etc. When a financial institution serves as an information provision institution, pieces of information of customers' balances, transaction records, etc. are collected, and analysis results representing usage of loans etc. are provided to information users such as a loan company etc.

The configurations of the information processing system 401 illustrated in FIG. 4, the information processing system 601 illustrated in FIG. 6, the information processing system 2301 illustrated in FIG. 23 and the information processing system 2501 illustrated in FIG. 25 are just exemplary, and some of the constituents may be omitted or changed in accordance with the purposes or conditions of the information processing systems. For example, in the information processing system 601 illustrated in FIG. 6, the backup storage device 631-2 may be omitted when the backup storage device 631-1 can accommodate the backup DB 653-2 and the backup DB 654-2.

The configuration of the server 632 illustrated in FIG. 7 is just exemplary, and some of the constituents may be omitted or changed in accordance with the purposes or conditions of the information processing system 601. The configuration of the VM 2524-i illustrated in FIG. 26 is just exemplary, and some of the constituents may be omitted or changed in accordance with purposes or conditions of the information processing system 2501.

The flowcharts illustrated in FIG. 5 and FIG. 24 and the operation sequences illustrated in FIG. 19 through FIG. 22C are just exemplary, and some of the processes may be omitted or changed in accordance with the configurations or conditions of the information processing systems. For example, when operations are not performed in mode M1, the operation sequences illustrated in FIG. 19 through FIG. 21 can be omitted, and when operations are not performed in mode M2, the sequences illustrated in FIG. 22A through FIG. 22C can be omitted.

The personal information illustrated in FIG. 8 and FIG. 9, the confidentializing item information illustrated in FIG. 10 and FIG. 11, the process table illustrated in FIG. 15, and the confidentialized personal information illustrated in FIG. 16 and FIG. 17 are just exemplary, and these pieces of information may change in accordance with the contents of personal information. The ID table illustrated in FIG. 12 is just exemplary, and an ID table in a different format may be used. For example, information such as a name, a health insurance card ID, etc., which are not national identification numbers, may be used as a personal ID. The time-date tables illustrated in FIG. 13, FIG. 14 and FIG. 27 are just exemplary, and a time-date-table in a different format may be used. The process of converting a data format illustrated in FIG. 18 is just exemplary, and the data format changes in accordance with the items.

Figure 28:
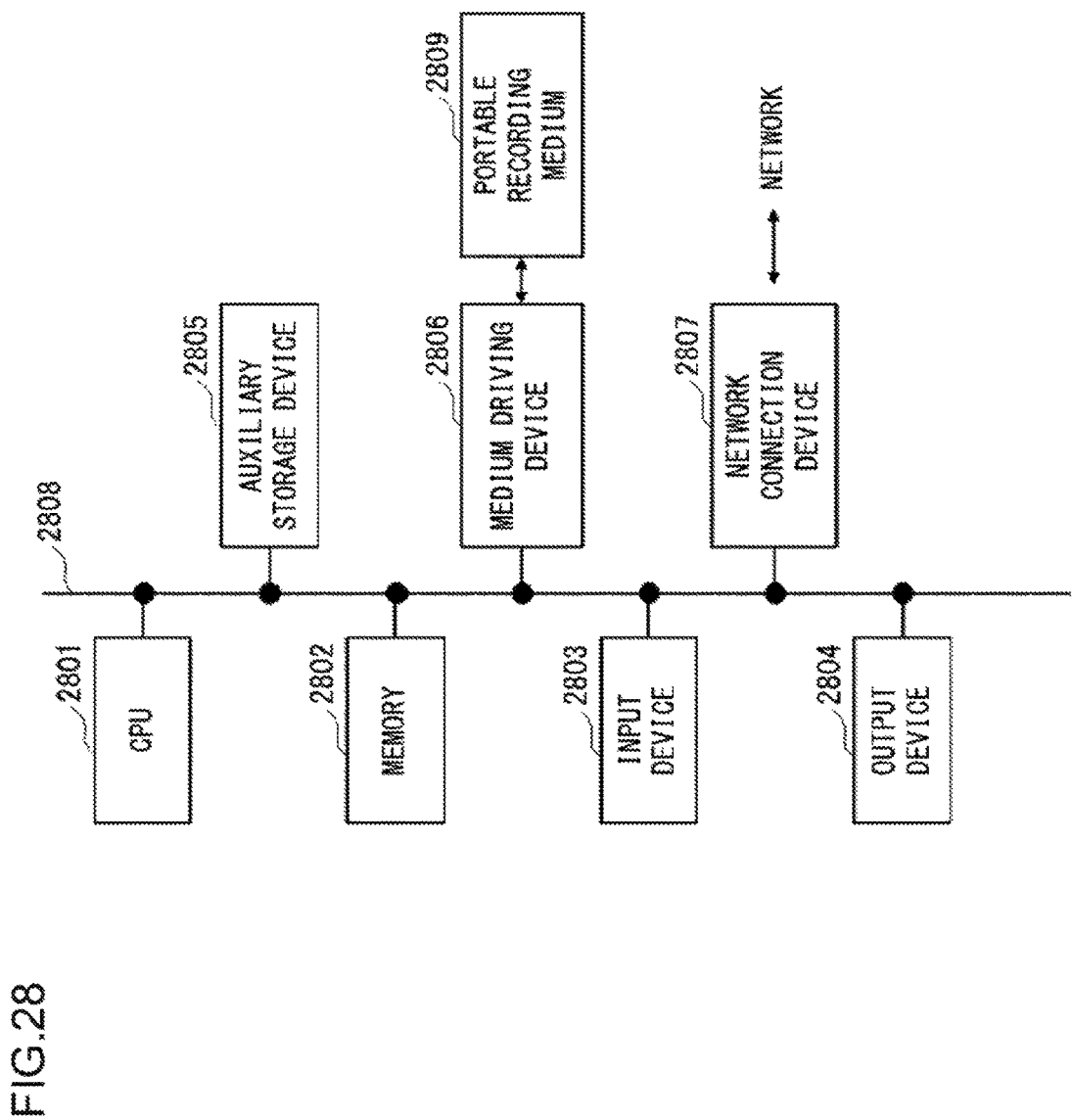
FIG. 28 illustrates a hardware configuration of an information processing apparatus.

FIG. 28 illustrates a hardware configuration example of an information processing apparatus that is used as the information processing apparatus 412 illustrated in FIG. 4, the server 632 illustrated in FIG. 7, the information processing apparatus 2312-j illustrated in FIG. 23, the server 2522-j illustrated in FIG. 25 and the server 2523 illustrated in FIG. 25. The information processing apparatus illustrated in FIG. 28 includes a Central Processing Unit (CPU) 2801, a memory 2802, an input device 2803, an output device 2804, an auxiliary storage device 2805, a medium driving device 2806 and a network connection device 2807. These constituents are connected to each other via a bus 2808.

The memory 2802 is for example a semiconductor memory such as a Read Only Memory (ROM), a Random Access Memory (RAM), a flash memory, etc., and stores a program and data used for processes. The memory 2802 can be used as the storage unit 421 illustrated in FIG. 4 and FIG. 7.

The CPU 2801 (processor) executes a program by using for example the memory 2802 so as to operate as the identification information assignment unit 422 and the confidentializing unit 423 illustrated in FIG. 4 and FIG. 7, and as the time-date management unit 701 illustrated in FIG. 7. The CPU 2801 executes a program by using the memory 2802 so as to operate also as the confidentializing unit 2322-j illustrated in FIG. 23 and the identification information assignment unit 2525 illustrated in FIG. 25. The CPU 2801 executes a program by using the memory 2802, and thereby makes the VM 2524-i illustrated in FIG. 26 operate.

The input device 2803 is for example a keyboard, a pointing device, etc., and is used for inputting instructions or information from the operator or the user. The output device 2804 is for example a display device, a printer, a speaker, etc., and is used for outputting inquiries to the operator or the user or for outputting process results.

The auxiliary storage device 2805 is for example a magnetic disk device, an optical disk device, a magneto-optical disk device, a tape device, etc. The auxiliary storage device 2805 may be a hard disk drive. The information processing apparatus can store a program and data in the auxiliary storage device 2805 beforehand so as to load them onto the memory 2802 and use them. The auxiliary storage device 2805 may be used as the storage unit 421 illustrated in FIG. 4 and FIG. 7.

The medium driving device 2806 drives a portable recording medium 2809 so as to access information recorded in it. The portable recording medium 2809 is a memory device, a flexible disk, an optical disk, a magneto-optical disk, etc. The portable recording medium 2809 may be a DVD, a Compact Disk Read Only Memory (CD-ROM), a Universal Serial Bus (USB) memory, etc. The operator or the user can store a program and data in the portable recording medium 2809 so as to load them onto the memory 2802 and use them.

As described above, a computer-readable recording medium that stores a program and data used for processes is a physical (non-transitory) recording medium such as the memory 2802, the auxiliary storage device 2805 or the portable recording medium 2809.

The network connection device 2807 is a communication interface that is connected to a communication network such as a LAN, a Wide Area Network (WAN), etc. so as to perform the conversion of data used for communications. The network connection device 2807 may be used as the transfer unit 702 illustrated in FIG. 7 and the reception unit 2321-*j* illustrated in FIG. 23. The information processing apparatus can receive a program and data from an external device via the network connection device 2807 and load them onto the memory 2802 so as to use them.

Note that it is not necessary for the information processing apparatus to include all the constituents illustrated in FIG. 28, and some of the constituents can be omitted in accordance with the purposes or conditions. For example, when it is not necessary to input instructions or information from the operator or the user, the input device 2803 can be omitted, and when it is not necessary to output inquiries to the operator or the user or to output process results, the output device 2804 can be omitted. When the portable recording medium 2809 is not used, the medium driving device 2806 can be omitted.

A similar information processing apparatus to that illustrated in FIG. 28 can be used as the PC 621-*i*, the PC 622-*i*, the server 623-*i*, the server 641 and the PC 642 illustrated in FIG. 6. An similar information processing apparatus to that illustrated in FIG. 28 may be used also as the server 2531 and the PC 2532 illustrated in FIG. 25.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An information processing apparatus, comprising:
a memory that stores common identification information shared between a plurality of information provision systems respectively of a plurality of information provision institutions for identifying a person;
a processor that is coupled to the memory, that assigns the common identification information to electronic personal information transferred to a storage device from a plurality of operation databases respectively in the plurality of information provision systems, and that generates confidentialized personal information by confidentializing the electronic personal information to which the common identification information has been assigned; and
a communication interface that transfers the confidentialized personal information to a collection storage device in an analysis system of an information analysis institution,
the storage device stores confidentializing item information that specifies an item as a confidentializing target from among a plurality of items included in the electronic personal information, and the processor confidentializes information of the item as the confidentializing target specified by the confidentializing item information,
the processor performs a first process of generating a plurality of pieces of confidentialized personal information respectively from a plurality of pieces of electronic personal information in accordance with a request from each of the plurality of information provision systems, and performs a second process of generating a plurality of pieces of confidentialized personal information respectively from a plurality of pieces of electronic personal information in accordance with a request from the analysis system, and
the processor interrupts the first process and starts the second process when the request is received from the analysis system after generating the confidentialized personal information from a specific piece of electronic personal information from among the plurality of pieces of electronic personal information in the first process, obtains a location of an interruption from progress information of a confidentializing process after completing the second process, and restarts the first process from a next piece of the electronic personal information following the specific piece of the electronic personal information indicated by the location of the interruption.

2. The information processing apparatus according to claim 1, wherein the memory stores a correspondence relationship that associates personal identification information included in the electronic personal information and the common identification information, and the processor assigns to the electronic personal information the common identification information associated with the personal identification information through the correspondence relationship, and confidentializes the personal identification information included in the electronic personal information.

3. The information processing apparatus according to claim 1, wherein the confidentializing item information specifies a first item as a target of a process of simplifying information and a second item as a target of a process of conversion into data indicating that information has been confidentialized, and the processor simplifies information of the first item included in the electronic personal information and converts information of the second item included in the electronic personal information into the data indicating that information has been confidentialized.

4. The information processing apparatus according to claim 1, wherein the processor converts a data format of the electronic personal information that is transferred from the plurality of operation databases into a uniform data format, and generates the confidentialized personal information from electronic personal information in the uniform data format when the plurality of operation databases use different data formats for electronic personal information.

5. The information processing apparatus according to claim 1, wherein the progress information includes first progress information and second progress information, and the processor performs the first process by referring to the first progress information, switches from the first progress information to the second progress information when the second process is started, performs the second process by referring to the second progress information and switches from the second progress information to the first progress information when the first process is restarted.

6. An information processing system comprising:
a storage device that stores electronic personal information that is transferred from a plurality of operation databases respectively in a plurality of information provision systems respectively of a plurality of information provision institutions, and confidentializing item information that specifies an item as a confidentializing target from among a plurality of items included in the electronic personal information; and
an information processing apparatus that assigns common identification information to the electronic personal information stored in the storage device, the common identification information being shared between the plurality of information provision systems for identifying a person, and that generates confidentialized personal information by confidentializing the electronic personal information to which the common identification information has been assigned,
the information processing apparatus confidentializes information of the item as the confidentializing target specified by the confidentializing item information,
the information processing apparatus performs a first process of generating a plurality of pieces of confidentialized personal information respectively from a plurality of pieces of electronic personal information in accordance with a request from each of the plurality of information provision systems, and performs a second process of generating a plurality of pieces of confidentialized personal information respectively from a plurality of pieces of electronic personal information in accordance with a request from an analysis system of an information analysis institution, and
the information processing apparatus interrupts the first process and starts the second process when the request is received from the analysis system after generating the confidentialized personal information from a specific piece of electronic personal information from among the plurality of pieces of electronic personal information in the first process, obtains a location of an interruption from progress information of a confidentializing process after completing the second process, and restarts the first process from a next piece of the electronic personal information following the specific piece of the electronic personal information indicated by the location of the interruption.

7. A non-transitory computer-readable recording medium having stored therein a program that causes a computer to execute a process comprising:
receiving common identification information from an identification information management device, the common identification information being shared between a plurality of information provision systems respectively of a plurality of information provision institutions for identifying a person;
setting the common identification information for electronic personal information transferred to a storage device from a plurality of operation databases respectively in the plurality of information provision systems; and
generating confidentialized personal information by confidentializing the electronic personal information for which the common identification information has been set,
the storage device stores confidentializing item information that specifies an item as a confidentializing target from among a plurality of items included in the electronic personal information, and the generating the confidentialized personal information confidentializes information of the item as the confidentializing target specified by the confidentializing item information,
the generating the confidentialized personal information performs a first process of generating a plurality of pieces of confidentialized personal information respectively from a plurality of pieces of electronic personal information in accordance with a request from each of the plurality of information provision systems, and performs a second process of generating a plurality of pieces of confidentialized personal information respectively from a plurality of pieces of electronic personal information in accordance with a request from an analysis system of an information analysis institution, and
the generating the confidentialized personal information interrupts the first process and starts the second process when the request is received from the analysis system after generating the confidentialized personal information from a specific piece of electronic personal information from among the plurality of pieces of electronic personal information in the first process, obtains a location of an interruption from progress information of a confidentializing process after completing the second process, and restarts the first process from a next piece of the electronic personal information following the specific piece of the electronic personal information indicated by the location of the interruption.

8. A non-transitory computer-readable recording medium having stored therein a program that causes a computer to execute a process comprising:
assigning common identification information to electronic personal information transferred to a storage device from a plurality of operation databases respectively in a plurality of information provision systems respectively of a plurality of information provision institutions, the common identification information being shared between the plurality of information provision systems for identifying a person; and
generating confidentialized personal information by confidentializing the electronic personal information to which the common identification information has been assigned,
the storage device stores confidentializing item information that specifies an item as a confidentializing target from among a plurality of items included in the electronic personal information, and the generating the confidentialized personal information confidentializes information of the item as the confidentializing target specified by the confidentializing item information, the generating the confidentialized personal information performs a first process of generating a plurality of pieces of confidentialized personal information respectively from a plurality of pieces of electronic personal information in accordance with a request from each of the plurality of information provision systems, and performs a second process of generating a plurality of pieces of confidentialized personal information respectively from a plurality of pieces of electronic personal information in accordance with a request from an analysis system of an information analysis institution, and the generating the confidentialized personal information interrupts the first process and starts the second process when the request is received from the analysis system after generating the confidentialized personal information from a specific piece of electronic personal information from among the plurality of pieces of electronic personal information in the first process, obtains a location of an interruption from progress information of a confidentializing process after completing the second process, and restarts the first process from a next piece of the electronic personal information following the specific piece of the electronic personal information indicated by the location of the interruption.

9. The non-transitory computer-readable recording medium according to claim 8, wherein the computer stores a correspondence relationship that associates personal identification information included in the electronic personal information and the common identification information, the assigning the common identification information assigns to the electronic personal information the common identification information associated with the personal identification information through the correspondence relationship, and the generating the confidentialized personal information confidentializes the personal identification information included in the electronic personal information.

10. An information processing apparatus comprising:

a memory;

a communication interface that is coupled to the memory and that receives common identification information from an identification information management device, the common identification information being shared between a plurality of information provision systems respectively of a plurality of information provision institutions for identifying a person; and a processor that is coupled to the memory and that sets the common identification information for electronic personal information transferred to a storage device from a plurality of operation databases respectively in the plurality of information provision systems, and that generates confidentialized personal information by confidentializing the electronic personal information for which the common identification information has been set, the storage device stores confidentializing item information that specifies an item as a confidentializing target from among a plurality of items included in the electronic personal information, and the processor confidentializes information of the item as the confidentializing target specified by the confidentializing item information, the processor performs a first process of generating a plurality of pieces of confidentialized personal information respectively from a plurality of pieces of electronic personal information in accordance with a request from each of the plurality of information provision systems, and performs a second process of generating a plurality of pieces of confidentialized personal information respectively from a plurality of pieces of electronic personal information in accordance with a request from an analysis system of an information analysis institution, and the processor interrupts the first process and starts the second process when the request is received from the analysis system after generating the confidentialized personal information from a specific piece of electronic personal information from among the plurality of pieces of electronic personal information in the first process, obtains a location of an interruption from progress information of a confidentializing process after completing the second process, and restarts the first process from a next piece of the electronic personal information following the specific piece of the electronic personal information indicated by the location of the interruption.

11. The information processing apparatus according to claim 10, wherein the identification information management device stores a correspondence relationship that associates personal identification information included in the electronic personal information and the common identification information, and assigns to the electronic personal information the common identification information associated with the personal identification information through the correspondence relationship, and the processor confidentializes the personal identification information included in the electronic personal information.

12. An information processing system comprising:

a plurality of storage devices that store electronic personal information transferred from a plurality of operation databases respectively in a plurality of information provision systems respectively of a plurality of information provision institutions, and confidentializing item information that specifies an item as a confidentializing target from among a plurality of items included in the electronic personal information;

an identification information management device that assigns common identification information to the electronic personal information stored in the plurality of storage devices, the common identification information being shared by the plurality of information provision systems for identifying a person; and a plurality of information processing apparatuses, each of the plurality of information processing apparatuses receives the common identification information from the identification information management device, sets the common identification information for the electronic personal information, and generates confidentialized personal information by confidentializing the electronic personal information for which the common identification information has been set, each of the plurality of information processing apparatuses confidentializes information of the item as the confidentializing target specified by the confidentializing item information, each of the plurality of information processing apparatuses performs a first process of generating a plurality of pieces of confidentialized personal information respectively from a plurality of pieces of electronic personal information in accordance with a request from each of the plurality of information provision systems, and performs a second process of generating a plurality of pieces of confidentialized personal information respectively from a plurality of pieces of electronic personal information in accordance with a request from an analysis system of an information analysis institution, and each of the plurality of information processing apparatuses interrupts the first process and starts the second process when the request is received from the analysis system after generating the confidentialized personal information from a specific piece of electronic personal information from among the plurality of pieces of electronic personal information in the first process, obtains a location of an interruption from prowess information of a confidentializing process after completing the second process, and restarts the first process from a next piece of the electronic personal information following the specific piece of the electronic personal information indicated by the location of the interruption.

* * * * *